(12) United States Patent
Chiou et al.

(10) Patent No.: US 11,020,358 B2
(45) Date of Patent: *Jun. 1, 2021

(54) METHOD FOR THE ANTI-SENESCENCE OF AND/OR REJUVENATING STEM CELLS

(71) Applicant: GWO XI STEM CELL APPLIED TECHNOLOGY CO., LTD., Zhubei (TW)

(72) Inventors: Tzyy-Wen Chiou, Zhubei (TW); Horng-Jyh Harn, Zhubei (TW); Shinn-Zong Lin, Zhubei (TW); Karthyayani Rajamani, Tamilnadu (IN); Yi-Chun Lin, Zhubei (TW)

(73) Assignee: GWO XI STEM CELL APPLIED TECHNOLOGY CO., LTD., Zhubei (TW)

( * ) Notice: Subject to any disclaimer, the term of this patent is extended or adjusted under 35 U.S.C. 154(b) by 169 days.

This patent is subject to a terminal disclaimer.

(21) Appl. No.: 15/593,141

(22) Filed: May 11, 2017

(65) Prior Publication Data

US 2017/0246123 A1 Aug. 31, 2017

Related U.S. Application Data

(62) Division of application No. 14/643,977, filed on Mar. 10, 2015, now abandoned.

(60) Provisional application No. 62/066,122, filed on Oct. 20, 2014.

(30) Foreign Application Priority Data

Dec. 11, 2014 (TW) .................................. 103143240

(51) Int. Cl.
*A61K 31/11* (2006.01)
*A61K 35/28* (2015.01)
*A61K 35/545* (2015.01)

(52) U.S. Cl.
CPC .............. *A61K 31/11* (2013.01); *A61K 35/28* (2013.01); *A61K 35/545* (2013.01)

(58) Field of Classification Search
None
See application file for complete search history.

(56) References Cited

U.S. PATENT DOCUMENTS

| 2007/0292401 A1 | 12/2007 | Harmon et al. |
| 2010/0041768 A1* | 2/2010 | Lee ...................... A61K 31/085 514/720 |
| 2012/0035126 A1 | 2/2012 | Duan et al. |
| 2014/0242020 A1 | 8/2014 | Meyer et al. |

FOREIGN PATENT DOCUMENTS

CN 104000752 8/2014

OTHER PUBLICATIONS

European Molecular Biology Laboratory chemical page (EMBL, ChEBI), CHEBI ID: 16731, cinnamaldehyde, http://www.ebi.ac.uk/chebi/searchId.do?chebild=CHEBI:16731 (Year: 2018).*
King et al, Antimutagenicity of cinnamaldehyde and vanillin in human cells: Global gene expression and possible role of DNA damage and repair, 2007, Mutation Research, 616: 60-69 (Year: 2007).*
Sperka et al, DNA damage checkpoints in stem cells, ageing and cancer, 2012, Nat Rev Mol Cell Biol., 13(9):579-9 (Year: 2012).*
Rho et al, Kojyl cinnamate ester derivatives promote adiponectin productionduring adipogenesis in human adipose tissue-derived mesenchymalstem cells 2014, Bioorganic & Medicinal Chemistry Letters, 24(9): 2141-2145 (Year: 2014).*
Hisha et al, Isolation and Identification of Hematopoietic Stem Cell—Stimulating Substances From Kampo (Japanese Herbal) Medicine, Juzen-Taiho-To, 1997, Blood, 90(3): 1022-1030; (Year: 1997).*
Sutton, M. T. et al., "Stem Cells: Innovations in Clinical Applications", Stem Cells International, 2014, vol. 2014, Article ID 516278, pp. 1-9.
Schallmoser, K. et al., "Replicative Senescence-Associated Gene Expression Changes in Mesenchymal Stromal Cells are Similar Under Different Culture Conditions", Haematologica, 2009, vol. 95(6), pp. 867-874.
Rodier, F. et al., "Four faces of cellular senescence", The Journal of Cell Biology, Feb. 2011, vol. 192(4), pp. 547-556.
Dimri, G. P. et al., "A biomarker that identifies senescent human cells in culture and in aging skin in vivo", Proceedings of the National Academy of Sciences of the United States of America, Sep. 1995, vol. 92(20), pp. 9363-9367.
Huang, J. et al., "SIRT1 Overexpression Antagonizes Cellular Senescence with Activated ERK/S6k1 Signaling in Human Diploid Fibroblasts", PLOS One, Mar. 2008, vol. 3(3), pp. 1-9.
Campisi, J., "Aging, tumor suppression and cancer: high wire-act!", Mechanisms of Ageing and Development, Jan. 2005, vol. 126(1), pp. 51-58.
Harley, C. B. et al., "Telomeres shorten during ageing of human fibroblasts", Nature, May 1990, vol. 345, pp. 458-460.

(Continued)

*Primary Examiner* — Sharmila G Landau
*Assistant Examiner* — Stephanie A McNeil
(74) *Attorney, Agent, or Firm* — Ping Wang; Morris, Manning & Martin LLP

(57) ABSTRACT

A method for the anti-senescence of and/or rejuvenating a stem cell is provided. The method comprising treating the stem cell with trans-cinnamaldehyde (TC). A kit is also provided. The kit comprising (1) a first part, comprising a stem cell; (2) a second part, comprising TC; and (3) a culture medium of the stem cell, placed in at least one of the first part, the second part, and a third part. In addition, a method for stem cell therapy is provided. The method comprising administering to a subject in need an effective amount of a stem cell, wherein the stem cell has been treated with TC before being administered.

4 Claims, 15 Drawing Sheets
(6 of 15 Drawing Sheet(s) Filed in Color)
Specification includes a Sequence Listing.

(56) References Cited

OTHER PUBLICATIONS

Choi, J. S. et al., "Coptis chinensis alkaloids exert anti-adipogenic activity on 3T3-L1 adipocytes by downregulating C/BP-α and PPAR-γ", Fitoterapia, Oct. 2014, vol. 98, pp. 199-208.
Harn, H. J. et al., "Adipose-Derived Stem Cells Can Abrogate Chemical-Induced Liver Fibrosis and Facilitate Recovery of Liver Function", Cell Transplantation, 2012, vol. 21(21), pp. 2753-2764.
Sun, L.M. et al., "Cinnamaldehyde Research and Applications", Guangdong Feed Journal, vol. 21, Dec. 2012, pp. 29-32 (English Abstract).
Wang, K. et al., "Redox homeostasis: the linchpin in stem cell self-renewal and differentiation", Cell Death and Disease, vol. 4(3), pp. 1-10.
Wondrak, G. T. et al., "The Cinnamon-derived Dietary Factor Cinnamic Aldehyde Activates the Nrf2-dependent Antioxidant Response in Human Epithelial Colon Cells", Molecules, 2010, vol. 15(5), pp. 3338-3355.
Chew, E. H. et al., "Cinnamaldehydes inhibit thioredoxin reductase and induce Nrf2: potential candidates for cancer therapy and chemoprevention", Free Radical Biology and Medicine, vol. 48(1), 2010, pp. 98-111.
Huang, T. C. et al., "Cinnamaldehyde Enhances Nrf2 Nuclear Translocation to Upregulate Phase II Detoxifying Enzyme Expression in HepG2 Cells", Journal of Agricultural and Food Chemistry, 2011, vol. 59(9), pp. 5164-5171.
Jiang, J. "Comparative study on growth and mechanism of cinnamaldehyde and citral anti-HL-60 cells", 2014 (English Abstract).

\* cited by examiner

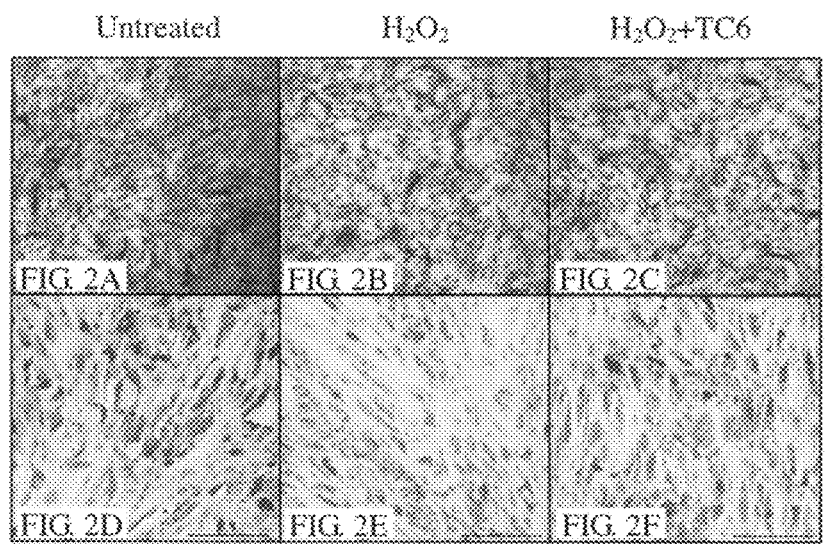
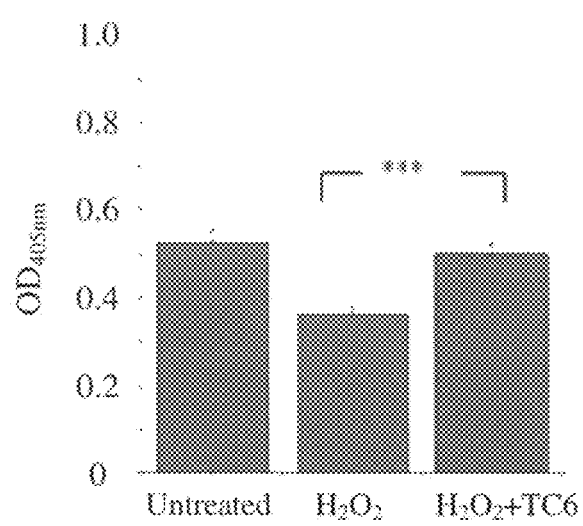
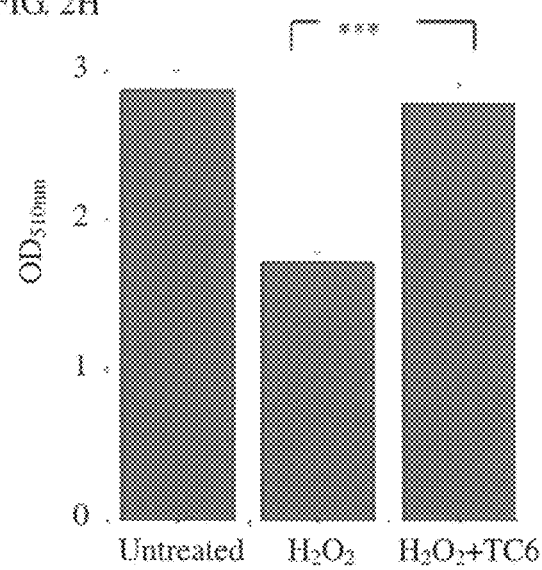
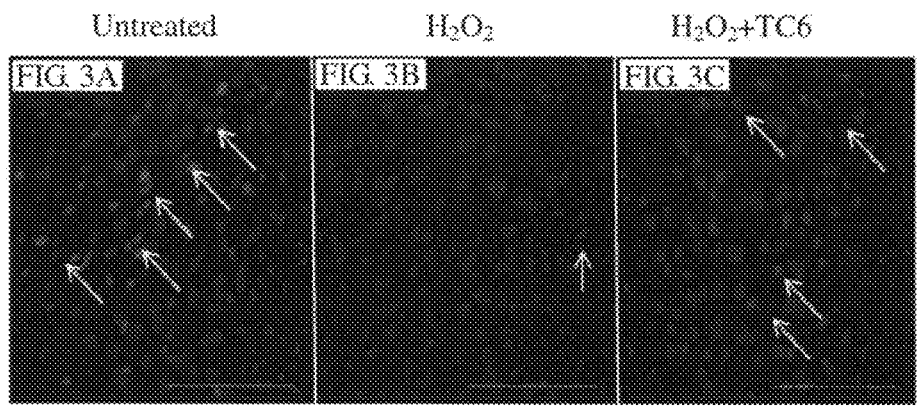

FIG. 4A
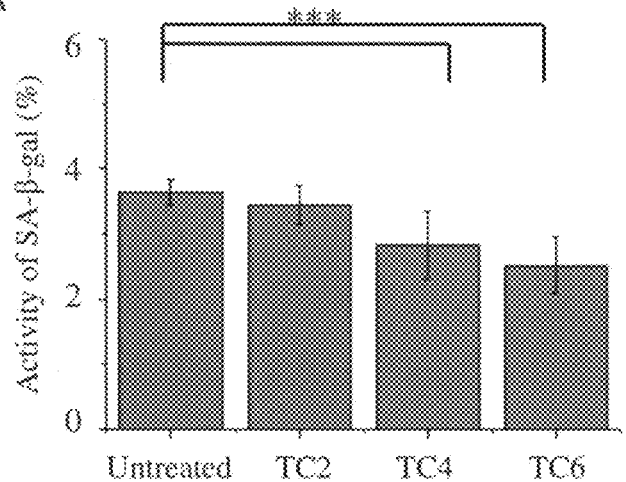
FIG. 4B
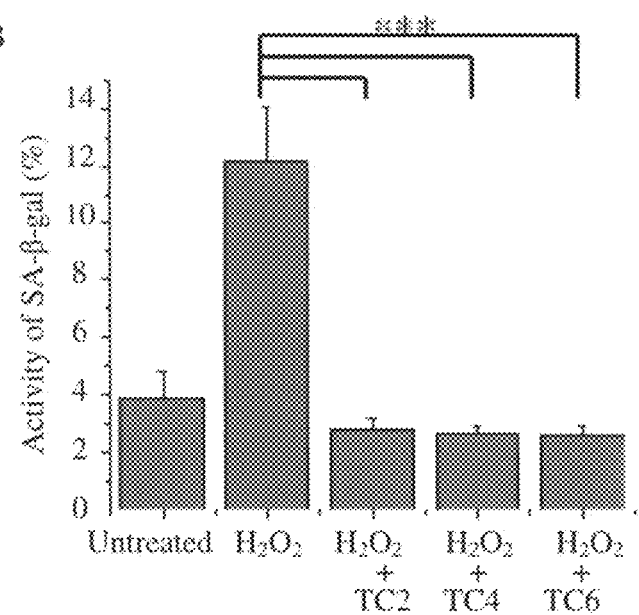
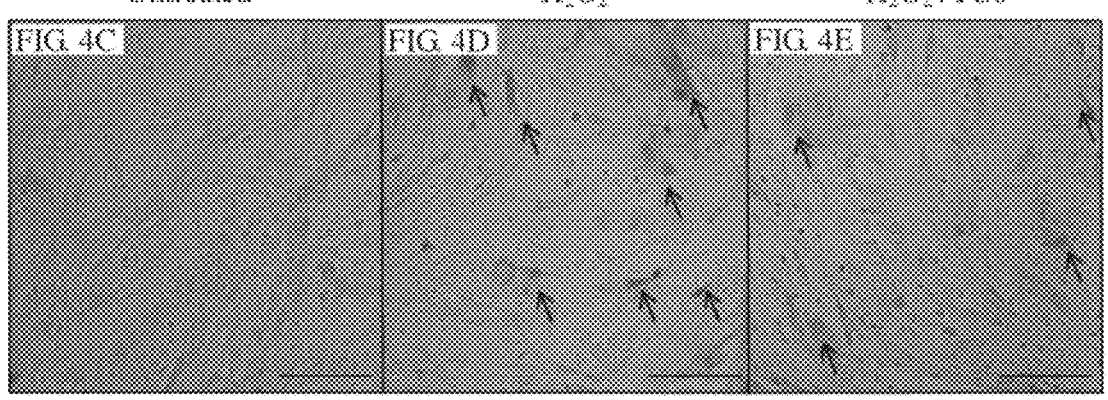

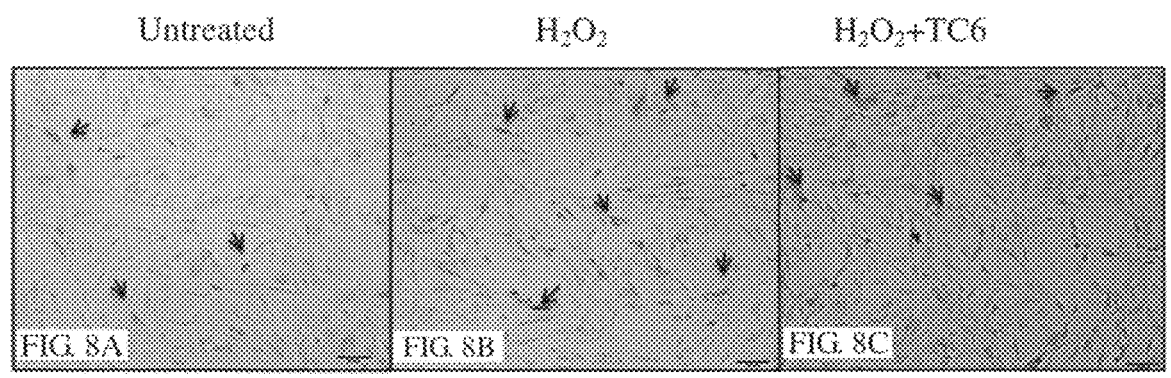
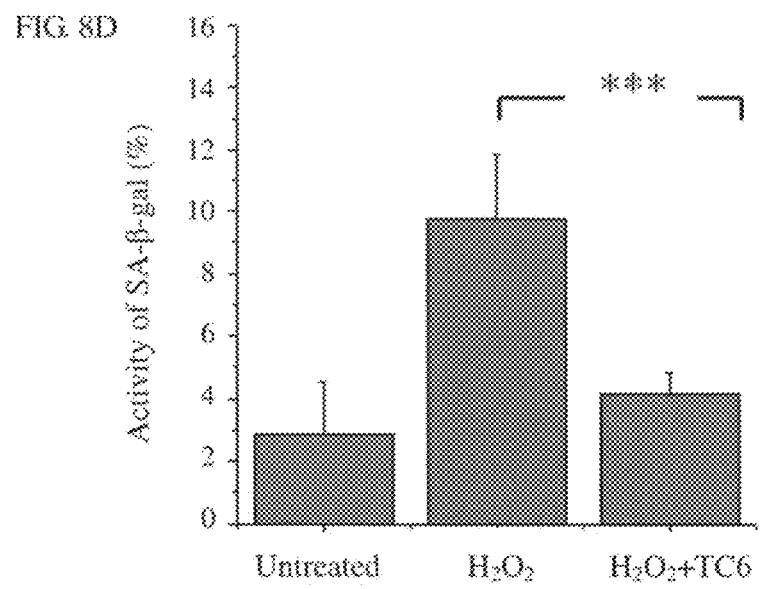

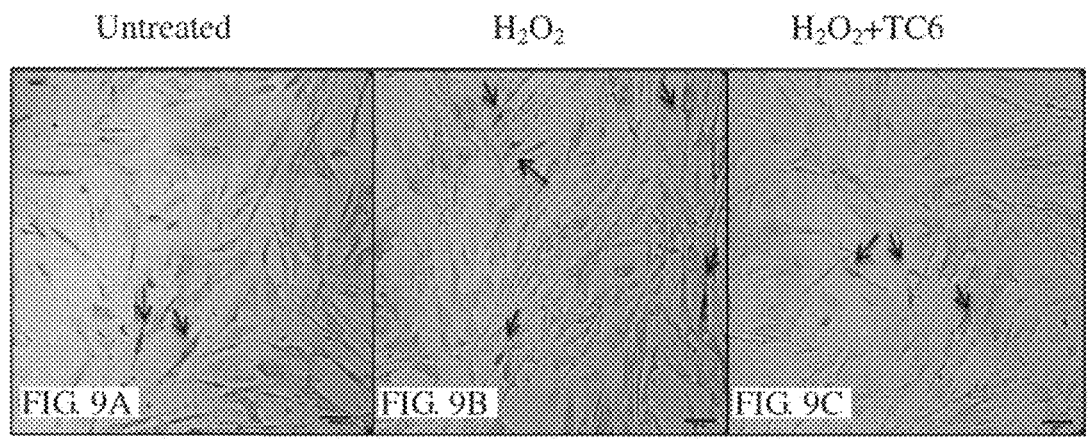
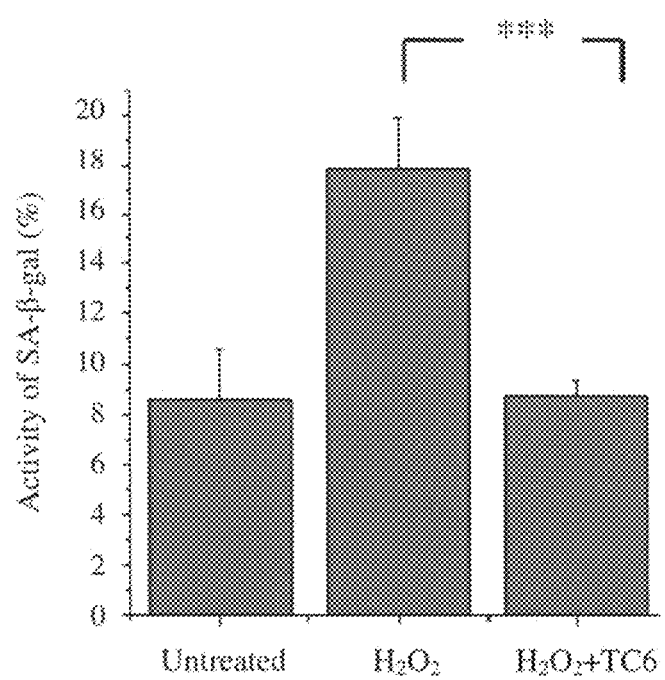

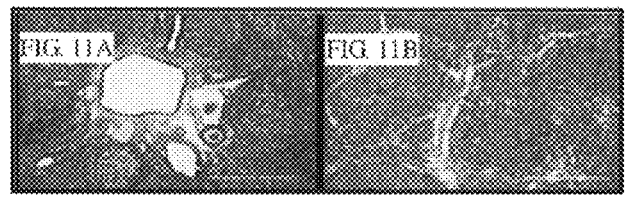
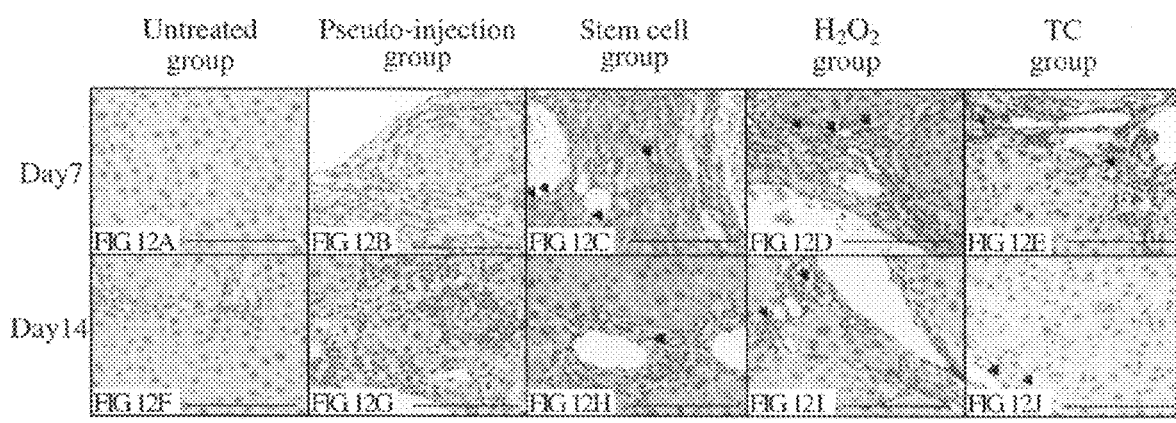
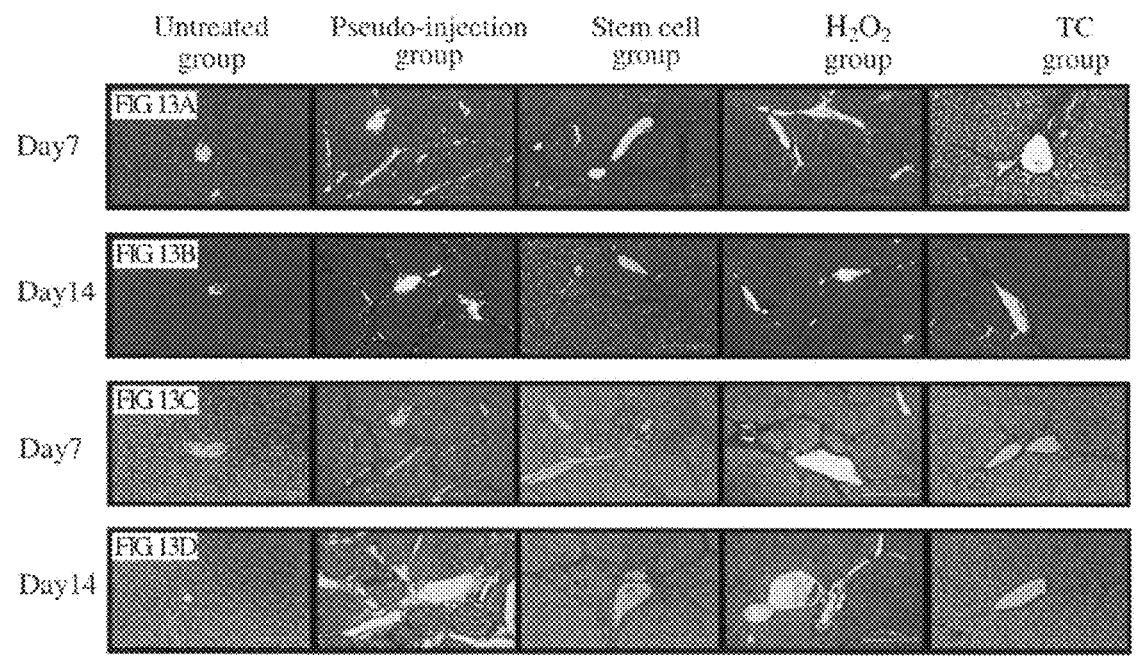

METHOD FOR THE ANTI-SENESCENCE OF AND/OR REJUVENATING STEM CELLS

This application is a Divisional of U.S. application Ser. No. 14/643,977, filed Mar. 10, 2015, which claims priority to U.S. Provisional Application Ser. No. 62/066,122 filed on Oct. 20, 2014, in the United States Patent and Trademark Office, and to Taiwan Patent Application No. 103143240 filed on Dec. 11, 2014, in the Taiwan Intellectual Property Office, the disclosures of which are incorporated herein in their entirety by reference.

BACKGROUND OF THE INVENTION

Field of the Invention

The present invention relates to the use of trans-cinnamaldehyde (TC), especially to the use of TC in stem cells, for such as the anti-senescence of stem cells and/or rejuvenating stem cells, and in stem cell therapy.

Descriptions of the Related Art

Stem cells, depending on their abilities to self-renew and to differentiate, can be classified into totipotent stem cells, pluripotent stem cells, multipotent stem cells and unipotent stem cells. Depending on the appearance order during the developmental process and distributional profile of stem cells, stem cells can be classified into embryonic stem cells (ES cells) and adult stem cells. The research results have shown that cell differentiation is reversible. By introducing specific genes into fully differentiated mature somatic cells, the mature somatic cells are induced to reprogram and form pluripotent cells with characteristics and functions similar to those of an embryonic stem cell, i.e., to form induced pluripotent stem cells (iPS cells). These iPS cells can differentiate into tissues of the human body, and thus, can be used in the research and therapy of diseases.

Currently, in the field of medical research, stem cell therapy brings hope to patients suffering from diseases which lack effective treatment, such as diabetes mellitus, autoimmune rejection, stroke, myocardial infarction, renal failure, leukemia, muscular dystrophy, severe anemia, Alzheimer's disease, Parkinson's disease, and cancers. The pluripotency of stem cells may solve the long-term difficulties encountered in the treatment of these diseases.

The success in transplanting stem cells into a human body to conduct stem cell therapy depends on the quality of stem cells. The reduction of the quality of stem cells including, for example, the cellular senescence induced by the impact of various stress signals, leads to a cell cycle arrest and a decrease in the proliferation rate in the stem cells, and thus, causes a lack of stem cells or progenitor cells which are essential for tissue repair, tissue regeneration and normal turnover. The above drawback is one of the major reasons for the poor efficiency of stem cell therapy. Therefore, if an approach that is effective in the anti-senescence of a stem cell is available, it would be able to enhance the success rate of stem cell therapy.

The present invention is a result of the research and development for the above needs. Inventors of the present invention found that trans-cinnamaldehyde (TC) is effective in the anti-senescence of stem cells, and is even able to rejuvenate stem cells. Thus, TC can be used in stem cell therapy to enhance the therapeutic effect thus provided.

SUMMARY OF THE INVENTION

An objective of the present invention is to provide a method for the anti-senescence of and/or rejuvenating a stem cell, comprising treating the stem cell with trans-cinnamaldehyde (TC). Preferably, the treatment is conducted in a culture medium of the stem cell at a TC concentration ranging from about 0.1 to about 50 µg per mL of the culture medium.

Another objective of the present invention is to provide a composition for the anti-senescence of and/or rejuvenating a stem cell, wherein the composition comprises TC.

Yet another objective of the present invention is to provide a use of TC in the manufacture of a preparation, wherein the preparation is for the anti-senescence of and/or rejuvenating a stem cell. Preferably, the preparation is a health food or a medicament.

Yet another objective of the present invention is to provide a kit, comprising (1) a first part, comprising a stem cell; (2) a second part, comprising TC; and (3) a culture medium of the stem cell, placed in at least one of the first part, the second part, and a third part. Preferably, the kit is used in stem cell therapy, wherein the stem cell is treated with TC in the culture medium of the stem cell before being administered.

Yet another objective of the present invention is to provide a method of stem cell therapy, comprising administering to a subject in need an effective amount of a stem cell, wherein the stem cell has been pre-treated with TC before being administered to the subject.

The detailed technology and preferred embodiments implemented for the present invention are described in the following paragraphs accompanying the appended drawings for people skilled in this field to well appreciate the features of the claimed invention.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 2A to 2C are pictures showing the osteogenic differentiation assay results of ADSCs without any treatment (untreated group), ADSCs treated with $H_2O_2$ ($H_2O_2$ group) and ADSCs treated with $H_2O_2$ and 6 µM of TC ($H_2O_2$+TC6 group);

FIGS. 2D to 2F are pictures showing the adipogenic differentiation assay results of ADSCs without any treatment (untreated group), ADSCs treated with $H_2O_2$ ($H_2O_2$ group) and ADSCs treated with $H_2O_2$ and 6 µM of TC ($H_2O_2$+TC6 group);

FIG. 2G is a statistical bar diagram showing the relative cell number after osteogenic differentiation of the group that ADSCs were not subjected to any treatment (untreated group), the group that ADSCs were subjected to the treatment of H2O2 ($H_2O_2$ group), and the group that ADSCs were subject to the treatment of $H_2O_2$ and 6 µM of TC ($H_2O_2$+TC6 group), wherein the vertical axis represents the absorbance at a wavelength of 450 nm (*** represents p value<0.01, reflecting a statistically significant difference);

FIG. 2H is a statistical bar diagram showing the relative cell number after adipogenic differentiation of the group that ADSCs were not subjected to any treatment (untreated group), the group that ADSCs were subjected to the treatment of H$_2$O$_2$ (H$_2$O$_2$ group), and the group that ADSCs were subjected to the treatment of H$_2$O$_2$ and 6 μM of TC (H$_2$O$_2$+TC6 group), wherein the vertical axis represents the absorbance at a wavelength of 510 nm (*** represents p value<0.01, reflecting a statistically significant difference);

FIGS. 3A to 3C are Ki67 staining pictures showing the proliferation rates of ADSCs without any treatment (untreated group), ADSCs treated with H$_2$O$_2$ (H$_2$O$_2$ group) and ADSCs treated with H$_2$O$_2$ and 6 μM of TC (H$_2$O$_2$+TC6 group);

FIG. 4A is a statistical bar diagram showing the activity of senescence associated-β-galactosidase (SA-β-gal) in ADSCs without any treatment (untreated group), ADSCs treated with 2 μM of TC (TC2 group), ADSCs treated with 4 μM of TC (TC4 group) and ADSCs treated with 6 μM of TC (TC6 group), wherein the vertical axis represents the activity percentage of SA-β-gal (*** represents p value<0.01, reflecting a statistically significant difference);

FIG. 4B is a statistical bar diagram showing the activity of SA-β-gal in ADSCs without any treatment (untreated group), ADSCs treated with H$_2$O$_2$ (H$_2$O$_2$ group), ADSCs treated with H$_2$O$_2$ and 2 μM of TC (H$_2$O$_2$+TC2 group), ADSCs treated with H$_2$O$_2$ and 4 μM of TC (H$_2$O$_2$+TC4 group) and ADSCs treated with H$_2$O$_2$ and 6 μM of TC (H$_2$O$_2$+TC6 group), wherein the vertical axis represents the activity percentage of SA-β-gal (*** represents p value<0.01, reflecting a statistically significant difference);

FIGS. 4C to 4E are pictures showing the activity of SA-β-gal in ADSCs without any treatment (untreated group), ADSCs treated with H$_2$O$_2$ (H$_2$O$_2$ group) and ADSCs treated with H$_2$O$_2$ and 6 μM of TC (H$_2$O$_2$+TC6 group);

FIGS. 8A to 8C are pictures showing the activity of SA-β-gal in human bone marrow mesenchymal stem cells (hBMMSCs) without any treatment (untreated group), hBMMSCs treated with H$_2$O$_2$ (H$_2$O$_2$ group) and hBMMSCs treated with H$_2$O$_2$ and 6 μM of TC (H$_2$O$_2$+TC6 group);

FIG. 8D is a statistical bar diagram showing the activity of SA-β-gal in hBMMSCs without any treatment (untreated group), hBMMSCs treated with H$_2$O$_2$ (H$_2$O$_2$ group) and hBMMSCs treated with H$_2$O$_2$ and 6 μM of TC (H$_2$O$_2$+TC6 group), wherein the vertical axis represents the percentage of the activity of SA-β-gal (*** represents p value<0.05, reflecting a statistically significant difference);

FIGS. 9A to 9C are pictures showing the activity of SA-β-gal in Wharton's jelly stem cells (WJSCs) without any treatment (untreated group), WJSCs treated with H$_2$O$_2$ (H$_2$O$_2$ group) and WJSCs treated with H$_2$O$_2$ and 6 μM of TC (H$_2$O$_2$+TC6 group);

FIG. 9D is a statistical bar diagram showing the activity of SA-β-gal in WJSCs without any treatment (untreated group), WJSCs treated with H$_2$O$_2$ (H$_2$O$_2$ group) and WJSCs treated with H$_2$O$_2$ and 6 μM of TC (H$_2$O$_2$+TC6 group), wherein the vertical axis represents the activity percentage of SA-β-gal (*** represents p value<0.05, reflecting a statistically significant difference);

FIG. 11A is a picture of the Masson's trichrome staining, showing the liver fibrosis degree of a liver fibrosis rat (i.e., a TAA rat);

FIG. 11B is a picture of the Hematoxylin and Eosin staining (H&E staining), showing the liver inflammation degree of a liver fibrosis rat (i.e., a TAA rat);

FIGS. 12A to 12E are pictures of the immunohistostaining performed using α-fetoprotein (AFP), showing the liver sections of the rat without any treatment (untreated group), the rat injected with normal saline (pseudo-injection group), the rat injected with "untreated group" ADSCs (stem cell group), the rat injected with "H$_2$O$_2$ group" ADSCs (H$_2$O$_2$ group), and the rat injected with "H$_2$O$_2$+TC6 group" ADSCs (TC group) at Day 7 post the different treatments;

FIGS. 12F to 12J are pictures of the immunohistostaining performed using AFP, showing the liver sections of the rat without any treatment (untreated group), the rat injected with normal saline (pseudo-injection group), the rat injected with "untreated group" ADSCs (stem cell group), the rat injected with "$H_2O_2$ group" ADSCs ($H_2O_2$ group), and the rat injected with "$H_2O_2$+TC6 group" ADSCs (TC group) at Day 14 post the different treatments;

FIGS. 13A and 13B are pictures of the Masson's trichrome staining, showing the liver fibrosis degree in the rat without any treatment (untreated group), the rat injected with normal saline (pseudo-injection group), the rat injected with "untreated group" ADSCs (stem cell group), the rat injected with "$H_2O_2$ group" ADSCs ($H_2O_2$ group), and the rat injected with "$H_2O_2$+TC6 group" ADSCs (TC group) at Day 7 post the different treatments (FIG. 13A) or Day 14 post the different treatments (FIG. 13B);

FIGS. 13C and 13D are pictures of the H&E staining showing the liver inflammation degree in the rat without any treatment (untreated group), the rat injected with normal saline (pseudo-injection group), the rat injected with "untreated group" ADSCs (stem cell group), the rat injected with "$H_2O_2$ group" ADSCs ($H_2O_2$ group), and the rat injected with "$H_2O_2$+TC6 group" ADSCs (TC group) at Day 7 post the different treatments (FIG. 13C) or Day 14 post the different treatments (FIG. 13D);

DESCRIPTION OF THE PREFERRED EMBODIMENT

Figure 1A:
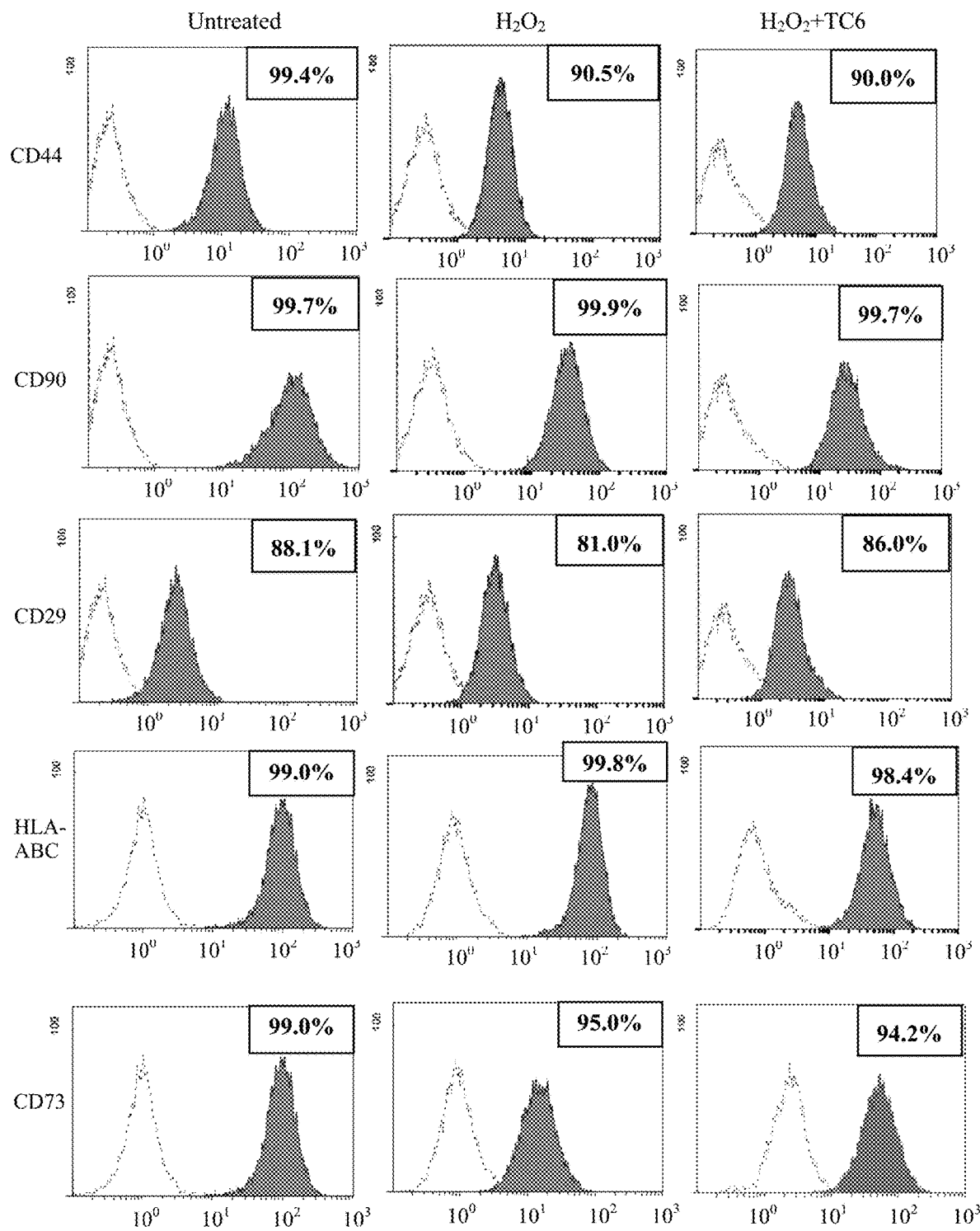
FIGS. 1A and 1B are diagrams of the flow cytometry analysis showing the expression profile of the surface antigens of adipose-derived stem cells (ADSCs) without any treatment (untreated group), ADSCs treated with $H_2O_2$ ($H_2O_2$ group) and ADSCs treated with $H_2O_2$ and 6 µM of TC ($H_2O_2$+TC6 group)

The following will describe some embodiments of the present invention in detail. However, without departing from the spirit of the present invention, the present invention may be embodied in various embodiments and should not be limited to the embodiments described in the specification. In addition, unless otherwise indicated herein, the expressions "a," "the," or the like recited in the specification of the present invention (especially in the claims) are intended to include the singular and plural forms. Furthermore, the term "effective amount" or "amount effective for treatment" used in this specification refers to the amount of the compound that can at least partially alleviate the condition that is being treated in a suspected subject when administered to the subject in need. The term "subject" used in this specification refers to a mammalian, including human and non-human animals.

Stem cells have been used widely by the present medicine, such applications include such as treating autoimmune diseases (e.g., diabetes mellitus and autoimmune rejection), treating digestive diseases (e.g., anus/digestive fistula diseases), treating hepatic diseases (e.g., hepatocirrhosis and hepatic fibrosis), treating renal diseases (e.g., renal failure), treating cardiovascular diseases (e.g., stroke and myocardial infarction), treating neurological diseases (e.g., Alzheimer's disease and Parkinson's disease), treating hematological diseases (e.g., leukemia), treating bone degeneration (e.g., degenerative arthritis, degeneration of knee cartilage), treating periodontitis, treating tendonitis, treating spinal injury, treating head trauma, plastic surgery (e.g., hemifacial atrophy and sunken scar), treating alopecia, whitening skin, and/or eliminating wrinkles. Relevant descriptions can be seen in, for example, "Stem cells: innovations in clinical applications. *Stem Cells int*. Volume 2014, Article ID 516278, 9 pages," which is entirely incorporated hereinto by reference.

However, after stem cells undergo several generations of subculture and/or have been transplanted into a subject's body, the cellular senescence caused by various stress signals will have an impact on the therapeutic effect of the stem cells. Relevant descriptions can be seen in, for example, "Replicative senescence-associated gene expression changes in mesenchymal stromal cells are similar under different culture conditions. *Haematologica*. 95(6):867-74 (2010)," which is entirely incorporated hereinto by reference. Research results have proven that stem cell senescence will be accompanied by the following actions: a decrease in the proliferation rate of stem cells, an increase in the activity of SA-β-gal in stem cells, a decrease in the expression level of SIRT1 gene in stem cells, and a decrease in the activity of telomerase in stem cells. It has also been proven that if the aforementioned actions can be reversed and/or recovered, stem cell senescence can be antagonized effectively, and this is favorable for the application of stem cells in treating diseases. Relevant descriptions can be seen in, for example, "Four faces of cellular senescence. *J Cell Biol*. 192(4):547-556 (2011);" "A biomarker that identifies senescent human cells in culture and in aging skin in vivo. *Proc Natl Acad Sci USA*. 92(20):9363-9367 (1995);" "SIRT1 overexpression antagonizes cellular senescence with activated ERK/S6k1 signaling in human diploid fibroblasts. *PLoS One*. 5; 3(3): e1710 (2008);" "Aging, tumor suppression and cancer: high wire-act! Mech Ageing Dev. 126(1):51-8 (2005);" and "Telomeres shorten during ageing of human fibroblasts. *Nature*. 345(6274):458-460 (1990)," which are entirely incorporated hereinto by reference.

Inventors of the present invention found that the treatment of stem cells with TC, wherein the stem cells show decreased proliferation rate, increased activity of SA-β-gal, decreased expression of SIRT1 gene and decreased activity of telomerase, would effectively reverse and/or recover the aforementioned actions in the stem cells. It has been further discovered that TC even can reduce the activity of SA-β-gal in general stem cells (i.e., non-senescent stem cells) and increase the expression level of SIRT1 gene in general stem cells.

Therefore, the present invention relates to the discovery of the anti-senescence of stem cells and rejuvenating stem cells and the uses thereof, including providing a composition, a preparation, and a method for the anti-senescence of stem cells and/or rejuvenating stem cells, wherein the preparation is manufactured with the use of TC, the composition comprises TC, and the method comprises treating stem cells with TC.

The composition, preparation, and method of the present invention can be used in any suitable stem cells and the examples of the stem cells include, for example, embryonic stem cells, adult stem cells, and induced pluripotent stem cells. The adult stem cells include such as hematopoietic stem cells and mesenchymal stem cells (e.g., ADSCs, BMMSCs, and WJSCs). Depending on the origin of the adult stem cells, the adult stem cells can be classified into such as umbilical cord blood stem cells, peripheral blood stem cells, neural stem cells, epithelial stem cells, muscle stem cells, adipose-derived stem cells, pancreas stem cells, limbal stem cells, hepatic stem cells, and intestinal stem cells.

According to the method of the present invention, if stem cells are pre-treated with TC before being used in a stem cell therapy, at least one of the following effects can be provided: improving the proliferation rate of the stem cells, reducing the activity of SA-β-gal in the stem cells, increasing the expression level of SIRT1 genes in the stem cells, and increasing the activity of telomere in the stem cells. Hence, the TC treatment is effective in the anti-senescence of stem cells and/or rejuvenating stem cells, and thus, enhances the effect of the said stem cell therapy. TC can be administered as a composition or a preparation.

In the method for the anti-senescence of stem cells and/or rejuvenating stem cells according to the present invention, stem cells can be treated with TC under any suitable conditions, as long as the conditions have no adverse effect on the stem cell survival. In one embodiment of the present invention, the TC treatment is conducted in a culture medium of the stem cells to be treated. The TC treatment could be conducted by adding TC and/or a TC-containing composition and/or a TC-containing preparation into a culture medium containing the stem cells to be treated. Alternatively, the treatment could be conducted by thawing rested and frozen stem cells and adding the stem cells into a TC-containing stem cell culture medium.

Any suitable stem cell culture medium can be used in the present invention, as long as the culture medium corresponds to the stem cells to be treated. The stem cell culture medium usually comprises components providing nutrients and conditions (e.g. pH) required for the growth and differentiation of the stem cells. In general, a stem cell culture medium comprises a base culture medium, an animal serum (e.g., fetal bovine serum), growth factors (e.g., human recombinant epidermal growth factor, fibroblast growth factor), nutrients (e.g., bovine pituitary extract), non-essential amino acids (NEAA) (e.g., L-glutamine, N-acetyl-L-cysteine), redox agents (e.g., L-ascorbic acid), antibiotics (e.g., penicillin, streptomycin), etc. Examples of the base medium suitable for the method of the present invention include, but are not limited to, K-SFM (Keratinocyte-Serum Free Medium), DMEM (Dulbecco's Modified Eagle's Medium), IMDM (Iscove's Modified Dulbecco's Medium), MEM (Minimum Essential Medium), α-MEM (α-Minimum Essential Medium), BME (Basal Media Eagle), MEM/F12 medium, Ham's F10 medium, Ham's F12 medium, and RPMI (Rosewell Park Memorial Institute). For instance, when the method of the present invention is used for the anti-senescence of ADSCs and/or rejuvenating ADSCs, K-SFM may be used as the base medium to conduct the TC treatment.

Preferably, the TC treatment is conducted in a stem cell culture medium at a TC concentration ranging from about 0.1 to about 50 μg per mL of the culture medium. It is more preferable that a TC concentration ranging from about 2 to about 20 μg per mL of the stem cell culture medium is used in the TC treatment to provide an effect of the anti-senescence of stem cells; and a TC concentration ranging from about 4 to about 20 μg per mL of the stem cell culture medium is used to provide an effect of rejuvenating stem cells.

The present invention also provides a composition for the anti-senescence of and/or rejuvenating a stem cell, and a use of TC in the manufacture of a preparation for the anti-senescence of a stem cell and/or rejuvenating a stem cell. The composition and preparation are those described hereinbefore and used in the method of the present invention. The composition and preparation can be provided for an in vitro treatment of stem cells to enhance the efficacy of the stem cells, and can be provided for being administered by a subject, such as human, to provide an effect of rejuvenating stem cells or the anti-senescence of stem cells in the subject.

When the composition/preparation for the anti-senescence of stem cells and/or rejuvenating stem cells according to the present invention is provided for an in vitro use, the composition/preparation can comprise a carrier, as long as the carrier has no adverse effect on the stem cells to be treated and will not affect the effect of the TC treatment. Examples of the carrier include, but are not limited thereto, dimethyl sulfoxide (DMSO), ethanol, and 0.5% methylcellulose-containing phosphate buffered saline (PBS).

When the composition or preparation for the anti-senescence of stem cells and/or rejuvenating stem cells according to the present invention is for being administered by a subject, such as human, the composition or preparation can be in any suitable form without particular limitations. For example, the composition or preparation can be manufactured as an edible product for swallowing or drinking, but is not limited thereby. Examples of the edible products include food additives, drink additives, dietary supplements, food constituents, drink constituents, health foods, nutraceutical products, medical foods, and nutriments. The composition or preparation can also be provided as medicaments. Preferably, the composition or preparation are provided as health foods or medicaments.

When the composition and/or preparation according to the present invention are provided as a medicament, the medicament can be in any suitable dosage form depending on the desired administration way. For example, the medicament can be administered by oral or parenteral (e.g., subcutaneous, intravenous, or nasal) to a subject in need, but is not limited thereby. Depending on the form and purpose, a suitable carrier can be chosen and used to provide the medicament.

As for the dosage form suitable for oral administration, the medicament provided by the present invention can comprise a pharmaceutically acceptable carrier that will not adversely affect the desired activity of TC. Examples of the carrier include such as solvents (e.g., water, saline, dextrose, glycerol, ethanol or its analogs, or a combination thereof), oily solvents, diluents, stabilizers, absorption retarders, disintegrants, emulsifiers, antioxidants, adhesives, lubricants, moisture absorbents, and solid carriers (e.g., starch and bentonite). The medicament can be provided in any suitable form for oral administration in any suitable manner, such as a tablet (includes a dragee), a pill, a capsule, a granule, a powder, a fluid extract, a solution, syrup, a suspension, an emulsion, a tincture, etc.

As for the dosage form of injection or drip suitable for subcutaneous, intravenous, intramuscular, or intraperitoneal administration, the medicament provided by the present invention can comprise one or more component(s) such as an isotonic solution, a saline buffer solution (e.g., a phosphate buffer solution or a citrate buffer solution), a solubilizer, an emulsifier, 5% sugar solution, and other carriers to provide the medicament as an intravenous injection, an emulsion intravenous injection, a powder injection, a suspension injection, or a powder-suspension injection. Alternatively, the medicament can be prepared as a pre-injection solid. The pre-injection solid can be provided in a dosage form which is soluble in other solutions or suspensions, or in an emulsifiable dosage form. A desired injection is provided by emulsifying the pre-injection solid or dissolving it in a solution or suspension prior to being administered by the subject in need. In addition, examples of the dosage form for external use which are suitable for nasal or transdermal administration include an emulsion, a cream, gel (e.g., an aquagel), paste (e.g., a dispersing paste and an ointment), a spray, or a solution (e.g., a washing liquid and a suspension).

Optionally, the medicament provided by the present invention may further comprise a suitable amount of additives, such as a flavoring agent, a toner, or a coloring agent for enhancing the taste and visual perception of the medicament, and/or an additional carrier, a binding agent, a buffering agent, a tackifying agent, a lubricant, a disintegrant, a stabilizer, an emulsifier, a dispersant, a suspending agent, a preservative, a conservative, an antibacterial agent, or an antifungal agent for improving the stability and storability of the medicament. In addition, the medicament may optionally further comprise one or more other active components or be used in combination with a medicament comprising the one or more other active components, to further enhance the effects of the medicament or to increase the application flexibility and adaptability of the preparation thus provided, as long as the other active components will not affect the desired effect of TC.

Depending on the requirements of the subject, the medicament provided by the present invention can be applied with various administration frequencies, such as once a day, several times a day or once every few days, etc. For example, when the medicament is applied orally for the anti-senescence of stem cells and/or rejuvenating stem cells, the dosage of the medicament is about 10 mg (as TC)/kg-body weight to about 500 mg (as TC)/kg-body weight per day, preferably about 60 mg (as TC)/kg-body weight to about 240 mg (as TC)/kg-body weight per day, and more preferably about 100 mg (as TC)/kg-body weight to about 160 mg (as TC)/kg-body weight per day, wherein the unit "mg/kg-body weight" means the dosage required per kg-body weight of the treated subject. However, for patients with severe stem cell senescence, the dosage can be increased to several times or several tens of times, depending on the practical requirements.

When the composition and/or preparation according to the present invention are provided as a health food, the health food may be in the form as dairy products, meat, breadstuff, vegetables, feeding stuffs, fruit juices, teas, sport drinks, and nutriceutical drinks, but is not limited thereby. Depending on the type of the health foods, different steps could be adopted for adding TC, as long as the operation will not affect the effect of the TC treatment. For example, TC could be added at the material stage of the health food manufacturing process (i.e., TC is a part of the health food), or TC could be added at the product stage after the health food manufacturing process has been completed (i.e., TC is an additive of the health food). Wherein, in the addition step, TC could be added by itself or be mixed with other components (e.g., proteins, sugars, fats, trace elements, or vitamins, but is not limited thereby) to manufacture the preparation as a tablet, a capsule, a granule, a powder, a suspension, or a emulsion prior to being added and mixed.

Optionally, the health food provided by the present invention may further comprise a suitable amount of an excipient (e.g., lactose, white sugar, starch, or mannitol), a disintegrant (e.g., calcium carbonate or calcium carboxymethyl cellulose), a binding agent (e.g., α-starch, Arabian gum, carboxymethyl cellulose, polyvinyl pyrrolidone, or hydroxypropyl cellulose), a tackifying agent (e.g., natural rubber), a lubricant (e.g., talcum powder, magnesium stearate, or polyethylene glycol 6000), and/or other additives (e.g., a flavoring agent, a toner, or a coloring agent for enhancing the taste and visual perception of the health food, and/or a carrier, a buffering agent, a stabilizer, an emulsifier, a dispersant, a suspending agent, a preservative, a conservative, an antibacterial agent, or antifungal agent for improving the stability and storability of the health food). In addition, the health food may optionally further comprise one or more other active components or be used in combination with a health food comprising the one or more other active components, to further enhance the effects of the health food or increase the application flexibility and adaptability of the preparation thus provided, as long as the other active components will not affect the desired effect of TC.

Depending on the age, body weight and healthy conditions of the subject, the health food provided by the present invention can be taken in various frequencies, such as once a day, several times a day or once every few days, etc. The amount of TC in the health food provided by the present invention can be adjusted, preferably to the amount should be taken daily, in light of the specific population. For example, if the recommended daily dosage for a subject is about 500 mg and each serving of the health food contains 250 mg of TC, the subject can take about two servings of the health food per day. The recommended daily dosage, use standards and use conditions for a specific population (e.g., pregnant woman and patients) and/or the recommendations for a use in combination with another food or medicament can be indicated on the exterior package of the health food provided by the present invention, and thus, is favorable for the user to take the health food by him- or herself safely and securely without the instructions of a doctor, pharmacist, or related executive.

According to the present invention, that pre-treatment of a stem cell with TC before using it in a stem cell therapy is effective in the anti-senescence of the stem cell and even can rejuvenate the stem cell, and can enhance the therapeutic effect of the stem cell. Therefore, the present invention also relates to the discovery and application of using TC in a stem cell therapy, and includes providing a kit and a method for stem cell therapy.

The kit for stem cell therapy according to the present invention comprises (1) a first part, comprising a stem cell; (2) a second part, comprising TC; and (3) a culture medium of the stem cell, placed in at least one of the first part, the second part, and a third part. When the kit is used in a stem cell therapy, the stem cell is treated with TC in the culture medium, and then the treated stem cell is used in the stem cell therapy. The selection of the stem cell and the culture medium, as well as the condition and method for using TC are all in line with the above descriptions. Preferably, TC is used at a concentration ranging from about 0.1 to about 50 µg per mL of the culture medium.

In the kit according to the present invention, the components are normally packaged and stored separately, and can be transported or sold separately or in a set. The kit may further contain an instruction manual, and thus, is favorable for the user to mix the components with each other at the customer's facility, to conduct the culture, treatment and administration of the stem cells according to the preset procedures and processes.

In one embodiment of the present invention wherein the components of the kit are separately packaged and stored and are separately transported or sold, the stem cells are kept in a preservation solution for freeze-storage in an environment at −80° C., TC is kept in a solvent (e.g., DMSO, ethanol and 0.5% methylcellulose-containing PBS) in a dark environment below 4° C., and the culture medium of the stem cells is kept in an environment at −20° C. In another embodiment of the present invention wherein the components of the kit are transported and sold in a set, the stem cells, TC and culture medium of the stem cells are separately kept in a container with an interior temperature of −80° C. (e.g., a liquid nitrogen tank), a container with an interior temperature of less than 4° C., and a container with an interior temperature of −20° C. (e.g., an ice box). There is no particular limitation for the shape and size of the containers, as long as the interior of each container is isolated from the environmental temperature such that the components, could be transported and sold in a set without affecting the preservation temperature of each other. Any suitable freezing medium could be used in the preservation of stem cells, as long as the components of the freezing medium could maintain the survival rate of stem cells effectively and do not affect the chromosome composition, proliferation and the differentiation capacity of the stem cells. Usually, the components of the freezing medium are adjusted depending on the corresponding stem cells. In general, the freezing medium includes DMSO, nutrients (e.g., glucose), pH regulators, etc., and does not include serum or animal proteins.

The method of stem cell therapy according to the present invention comprises administering to a subject in need an effective amount of a stem cell, wherein the stem cell has been pre-treated with TC before being administered to the subject. For example, in one embodiment of the method of stem cell therapy according to the present invention, stem cells are treated with TC before being used in the stem cell therapy of liver fibrosis. Such TC treatment is effective in the anti-senescence of the stem cells and thus can enhance the effect of the stem cells on treating liver fibrosis. The treatment of stem cells, selection of materials, dosage of TC for administration, and the application in relative therapy are all in line with the above descriptions.

The present invention will be further illustrated in detail with specific examples as follows. However, the following examples are provided only for illustrating the present invention, and the scope of the present invention is not limited thereby.

EXAMPLES

A. Cellular Experiments

[Example 1] Preparation of Stem Cells (1) Adipose Stem Cells (ADSCs)

ADSCs were sub-cultured for 5 to 7 passages in K-SFM (Keratinocyte-Serum Free Medium, purchased from Invitrogen-Gibco) at 37° C. under 5% $CO_2$. The K-SFM contained human recombinant epidermal growth factor (purchased from Gibco), bovine pituitary extract (purchased from Invitrogen-Gibco), 10% of fetal bovine serum (FBS; purchased from Hyclone), 1% of penicillin/streptomycin (P/S; purchased from Biowest), 0.2 mM of L-ascorbic acid (purchased from Sigma), and 2 mM of N-acetyl-L-cysteine (purchased from Sigma).

Four portions of equal volume of the above culture medium containing the sub-cultured ADSCs were separately handled by adding thereinto $H_2O_2$ (purchased from Sigma-Aldrich) at a final concentration of 100 μM and reacting for 2 hours to induce senescence of the ADSCs, replacing the culture medium with a fresh culture medium, adding thereinto TC (trans-cinnamaldehyde, purchased from Sigma-Aldrich) at a final concentration of 0, 2, 4 or 6 μM and reacting for 6 hours, so as to obtain "$H_2O_2$ group (i.e., treated with $H_2O_2$ for 2 hours, but not treated with TC)," "$H_2O_2$+TC2 group (i.e., treated with $H_2O_2$ for 2 hours and then treated with 2 μM of TC for 6 hours)," "$H_2O_2$+TC4 group (i.e., treated with $H_2O_2$ for 2 hours and then treated with 4 μM of TC for 6 hours)," and "$H_2O_2$+TC6 group (i.e., treated with $H_2O_2$ for 2 hours and then treated with 6 μM of TC for 6 hours)" ADSCs.

Five portions of equal volume of the above culture medium containing the sub-cultured ADSCs were separately handled by adding thereinto with $H_2O_2$ at a final concentration of 100 μM and reacting for 2 hours to induce senescence of the ADSCs. Then, the culture medium in each of the five portions was replaced with a fresh culture medium. The first portion was handed by adding thereinto TC at a final concentration of 6 μM and reacting for 6 hours to obtain "TC6H group" ADSCs. The second to fifth portions were handled by adding thereinto TC at a final concentration of 6 μM, reacting for 6 hours, and then transferring and incubating the ADSCs in DMEM for 12, 24, 48 and 72 hours respectively to obtain "TC12H group," "TC24H group," "TC48H group" and "TC72H group" ADSCs.

Four portions of equal volume of the above culture medium containing the sub-cultured ADSCs were handled by adding thereinto TC at final concentrations of 0, 2, 4 and 6 μM respectively, and reacting for 6 hours to obtain "untreated group (i.e., without any treatment)," "TC2 group (i.e., treated only with 2 μM of TC)," "TC4 group (i.e., treated only with 4 μM of TC)" and "TC6 group (i.e., treated only with 6 μM of TC)" ADSCs.

(2) Wharton's Jelly Stem Cells (WJSCs)

WJSCs were sub-cultured for 5 to 7 passages in IMDM (Iscove's Modified Dulbecco's Medium, purchased from Invitrogen) at 37° C. under 5% $CO_2$, wherein the IMDM contained 10% of FBS (purchased from Hyclone), 10 μg/mL of basic fibroblast growth factor (bFGF; purchased from R&D system), 2 mM of L-glutamine (purchased from Invitrogen-Gibco), and 100 Units/mL of penicillin/streptomycin (purchased from Invitrogen).

Three portions of equal volume of the above culture medium containing the sub-cultured WJSCs were provided. The first and second portions were handled by adding thereinto $H_2O_2$ at a final concentration of 100 μM, reacting for 2 hours to induce senescence of the WJSCs, replacing the culture medium with a fresh culture medium, adding thereinto TC at final concentrations of 0 and 6 μM, respectively, and reacting for 6 hours to obtain "$H_2O_2$ group (i.e., treated with $H_2O_2$ for 2 hours, but not treated with TC)" and "$H_2O_2$+TC6 group (i.e., treated with $H_2O_2$ for 2 hours and then treated with 6 μM of TC for 6 hours) WJSCs. The third portion without any treatment was referred to as "untreated group" WJSCs.

(3) Human Bone Marrow Mesenchymal Stem Cells (hBMMSCs)

hBMMSCs were sub-cultured for 5 to 7 passages in IMDM (purchased from Invitrogen-Gibco) at 37° C. under 5% $CO_2$, wherein the IMDM contained 10% of FBS (purchased from Hyclone), 10 μg/mL of bFGF (purchased from R&D system), 2 mM of L-glutamine (purchased from Invitrogen-Gibco), and 100 Units/mL of penicillin/streptomycin (purchased from Invitrogen-Gibco).

Three portions of equal volume of the above culture medium containing the sub-cultured hBMMSCs were provided. The first and second portions were handled by adding thereinto $H_2O_2$ at a final concentration of 100 μM, reacting for 2 hours to induce senescence of the hBMMSCs, replacing the culture medium with a fresh culture medium, adding thereinto TC at final concentrations of 0 and 6 μM respectively, and reacting for 6 hours to obtain "$H_2O_2$ group (i.e., treated with $H_2O_2$ for 2 hours, but not treated with TC)" and "$H_2O_2$+TC6 group (i.e., treated with $H_2O_2$ for 2 hours and then treated with 6 μM of TC for 6 hours) hBMMSCs. The third portion without any treatment was referred to as "untreated group" hBMMSCs.

[Example 2] Effects of $H_2O_2$ and TC on the Expression of the Surface Antigens of Stem Cells Samples of the "untreated group," "$H_2O_2$ group," and "$H_2O_2$+TC6 group" ADSCs obtained from Example 1 (1) were labelled with the following antibodies: an antibody against human cluster of differentiation 14 (CD14), an antibody against human cluster of differentiation 29 (CD29), an antibody against human cluster of differentiation 44 (CD44), an antibody against human cluster of differentiation 45 (CD45), and an antibody against human leukocyte antigen-ABC (HLA-ABC) (purchased from Dako Ltd.); an antibody against human cluster of differentiation 34 (CD34), an antibody against human cluster of differentiation 49b (CD49b), an antibody against human cluster of differentiation 73 (CD73), an antibody against human cluster of differentiation 90 (CD90), and an antibody against human leukocyte antigen-DR (HLA-DR) (purchased from Becton Dickinson Ltd.). Then, the expressions of the surface antigens of the cells in each group were analyzed by a flow cytometer (Beckman Coulter Ltd., FC500). The results are shown in FIGS. 1A and 1B.

Figure 1B:
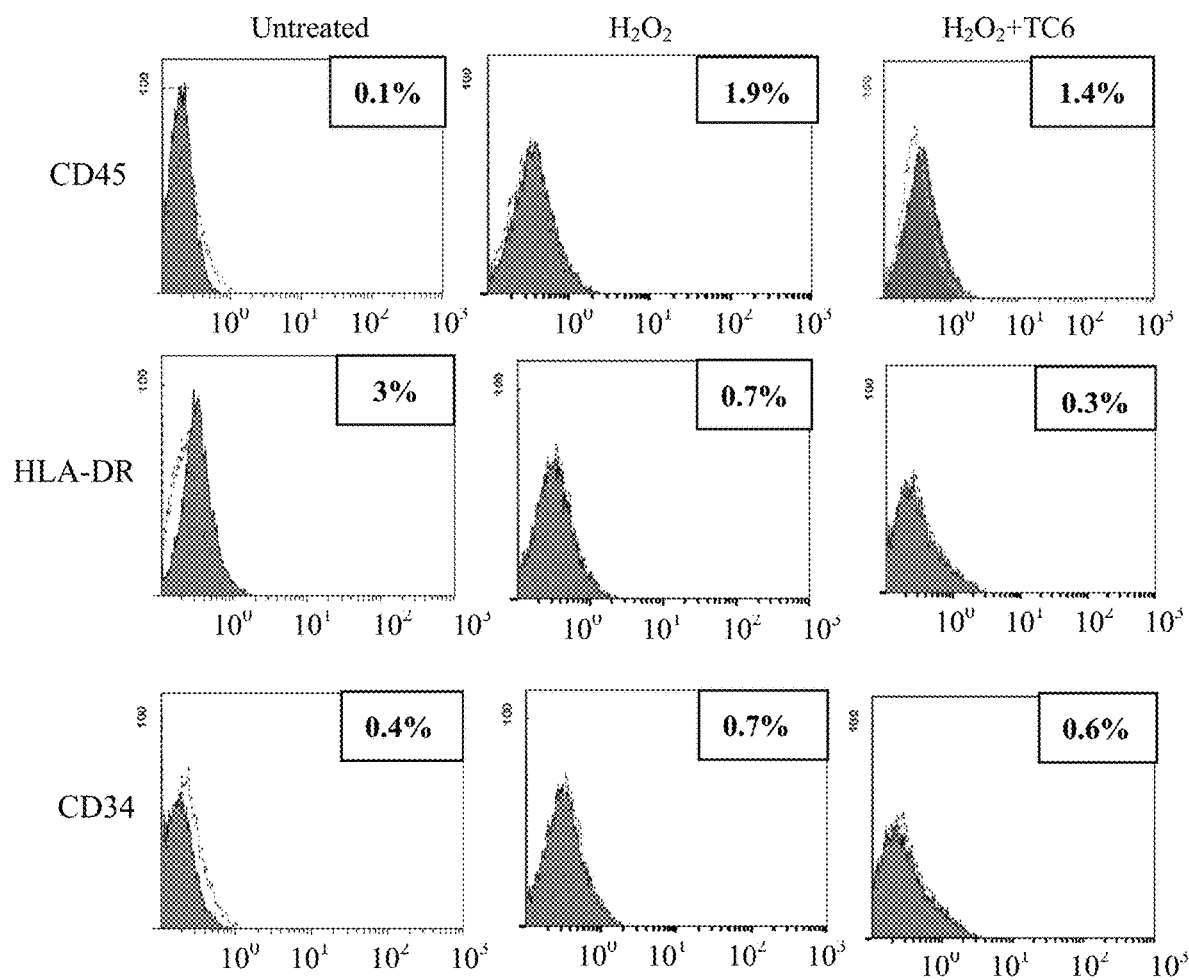

As shown in FIGS. 1A and 1B, as compared to the "untreated group" ADSCs, the expression phenotypes of the surface antigens of the "$H_2O_2$ group" and "$H_2O_2$+TC6 group" ADSCs were not significantly changed. These three groups of ADSCs all expressed the mesenchymal stem cell markers (e.g., CD29, CD44, CD73, CD90 and HLA-ABC), but did not express the hematopoietic stem cell markers (e.g., CD34, CD45 and HLA-DR). The aforementioned results indicate that neither the $H_2O_2$ treatment nor the TC treatment will affect the expressions of the surface antigens of stem cells.

[Example 3] Effect of TC on the Differentiation Capacity of Stem Cells

Experiment (1) Osteogenic Differentiation Assay

Samples of the "untreated group," "$H_2O_2$ group," and "$H_2O_2$+TC6 group" ADSCs obtained from Example 1 (1) were cultured in DMEM to induce osteogenic differentiation, wherein the DMEM contained 10% of FBS, 20 nM of dexamethasone, 100 Units/mL of penicillin, 100 μg/mL of streptomycin, 2.5 μg/mL of amphotericin, 10 mM of b-glycerophosphate, and 0.05 mM of L-ascorbic acid 2-phosphate. After being cultured for 7 days, the samples were stained with an alkaline phosphatase detection kit (purchased from EMD Millipore, CSCR004) and then photographed by a microscope. The results are shown in FIGS. 2A to 2C, wherein the cells after the osteogenic differentiation were in purple color under the microscope. After being photographed, the absorbance at a wavelength of 450 nm (i.e., $OD_{450}$) of each sample was measured to figure out the effect of $H_2O_2$ and/or TC on the osteogenic differentiation capacity of ADSCs. The results are shown in FIG. 2G.

As shown in FIGS. 2A to 2C and 2G, as compared to "untreated group," the cell number after the osteogenic differentiation of ADSCs in "$H_2O_2$ group" was significantly reduced, and the cell number in "$H_2O_2$+TC6 group" was similar to that in "untreated group." The aforementioned results indicate that the $H_2O_2$ treatment would reduce the osteogenic differentiation capacity of stem cells, while such disadvantageous effect of $H_2O_2$ could be offset by the TC treatment, and thus, TC treatment can make the osteogenic differentiation capacity of stem cells recover to a normal level.

Experiment (2) Adipogenic Differentiation Assay

Samples of the "untreated group," "$H_2O_2$ group," and "$H_2O_2$+TC6 group" ADSCs obtained from Example 1 (1) were cultured in DMEM to induce adipogenic differentiation, wherein the DMEM contained 10% of FBS, 10 μg/mL of insulin, 1 μM of dexamethasone, 0.5 mM of 3-isobutyl-1-methylxanthine (IBMX), and 100 μM of indomethacin. After being cultured for 7 days, the samples were stained by Oil Red O staining and then photographed by a microscope. The results are shown in FIGS. 2D to 2F. When stem cells undergo adipogenic differentiation, oil droplets will produce in the cells, and the oil droplets appear orange-red color under the microscope. The steps of Oil Red O staining can be seen in "*Coptis chinensis* alkaloids exert anti-adipogenic activity on 3T3-L1 adipocytes by downregulating C/EBP-α and PPAR-γ. *Fitoterapia*. 98:199-208 (2014)," which is entirely incorporated hereinto by reference.

After being photographed, the oil droplets were extracted from the cells in each sample with isopropanol containing 4% Nonidet P-40. The absorbance of the oil droplets at a wavelength of 510 nm (i.e., $OD_{510}$) of each sample were measured, wherein the absorbance corresponds to the number of cells in orange-red color (i.e., cells present after adipogenic differentiation). The results are shown in FIG. 2H.

As shown in FIGS. 2D to 2F and 2H, as compared to "untreated group," the cell number after the adipogenic differentiation of ADSCs in "$H_2O_2$ group" was significantly reduced, and the cell number in "$H_2O_2$+TC6 group" was similar to that in "untreated group." The aforementioned results indicate that the $H_2O_2$ treatment would reduce the adipogenic differentiation capacity of stem cells, while the disadvantageous effect of $H_2O_2$ could be offset by the TC treatment, and thus, TC treatment can make the adipogenic differentiation capacity of stem cells recover to a normal level.

[Example 4] Effects of TC on Rejuvenating Stem Cells and on the Anti-Senescence of Stem Cells Experiment (1) Analysis of Proliferation Rate Samples of the "untreated group," "$H_2O_2$ group," and "$H_2O_2$+TC6 group" ADSCs obtained from Example 1 (1)

were washed with phosphate buffered saline (PBS) twice, fixed with 3.7% formaldehyde, and blocked with 10% FBS (diluted in PBS). Then, the cells of each sample were washed with PBS once, and reacted with a Ki67 antibody (purchased from Novus biological) at 4° C. overnight. Thereafter, the cells were washed with PBS once, and reacted with a secondary antibody (goat anti rabbit IgG, purchased from Merk Millpore) at room temperature for 2 hours. The cells were then stained with DAPI (purchased from Invitrogen) in the dark, and then observed by a fluorescent microscope. The results are shown in FIGS. 3A to 3C. Because the Ki67 antibody can label the nucleoproteins in cells at G1, S, G2 and M phases, but not cells at G0 phase, more cells labeled by the Ki67 antibody (hereinafter referred as to Ki67-positive cells) indicates more proliferating cells (i.e., a higher proliferation rate).

As shown in FIGS. 3A to 3C, as compared to "untreated group," the number of the Ki67-positive cells in "$H_2O_2$ group" were significantly reduced, and the number of the Ki67-positive cells in "$H_2O_2$+TC6 group" was increased to be similar to that in "untreated group" (the arrows in the Figures indicate the proliferating cells). The aforementioned results indicate that the $H_2O_2$ treatment would lead to senescence of stem cells, while the disadvantageous effect of $H_2O_2$ could be offset by the TC treatment, and thus, TC treatment can make the proliferation rate of the senescent stem cells recover to a normal level (i.e., TC is effective in the anti-senescence of stem cells).

Experiment (2) Senescence Associated-β-Galactosidase (SA-β-Gal) Activity Assay

It has been known that senescent cells in acidic environment (e.g., pH 6.0) show the activity of SA-β-gal. Therefore, the senescence level of cells can be reflected by measuring the expression level of SA-β-gal in the cells.

The ADSCs in each sample of the group obtained from Example 1 (1) were washed with PBS twice, fixed with 3% formaldehyde and washed with PBS once. Then, the ADSCs were stained with a fresh staining solution at 37° C. under no $CO_2$ for 12 hours, wherein the staining solution comprised 1 mg/mL of 5-bromo-4-chloro-3-indolyl-β-D-galactosidase (X-gal), 40 mM of citric acid/sodium phosphate (pH 6.0), 5 mM of potassium ferrocyanide, 5 mM of potassium ferricyanide, 150 mM of sodium chloride, and 2 mM of magnesium chloride.

The staining solution was removed. The ADSCs in each sample were washed with PBS. The cells were observed and photographed under a microscope with 10-fold magnification, and the percentage of SA-β-gal activity-positive cells was calculated. The results are shown in FIGS. 4A to 4E.

As shown in FIG. 4A, as compared to "untreated group," the number of the SA-β-gal activity-positive cells in "TC2 group," "TC4 group" and "TC6 group" were significantly reduced along with the increment in the concentration of TC. The results suggest that TC is effective in rejuvenating stem cells.

As shown in FIGS. 4B to 4E, as compared to "untreated group," the number of the SA-β-gal activity-positive cells in "$H_2O_2$ group" was significantly increased. These results indicate that $H_2O_2$ would lead to the senescence of stem cells. In addition, as compared to "$H_2O_2$ group," the number of the SA-β-gal activity-positive cells in "$H_2O_2$+TC2 group," "$H_2O_2$+TC4 group" and "$H_2O_2$+TC6 group" were significantly reduced. These results indicate that TC could offset the disadvantageous effect caused by $H_2O_2$ on the senescence of stem cells.

Experiment (3) Analysis of Gene Expression (3-1) Preparation of cDNA

The total cellular RNA of the ADSCs, BMMSCs and WJSCs in each sample of the group obtained from Example 1 (1) were extracted with an RNeasy Mini kit (purchased from Qiagen), and then reverse transcribed into cDNA by a reverse transcription kit (RT Pre Mix, purchased from iNtRON Biotechnology).

(3-2) Quantitative RT-PCR

Each of the cDNA of ADSCs of different groups from Experiment (3-1) was handled as follows. 1 μl of the cDNA of ADSCs was mixed with 0.6 μl of forward primer (5 pmole/μl) and 0.6 μl of reverse primer (5 pmole/μl) of SIRT1 gene as shown in Table 1 (i.e., SEQ No. 1 and SEQ No. 2), 3.4 μl of deionized water, and 10 μl of SYBR Green PCR Master Mix (purchased from Thermo Scientific). The mixture was then placed in a real-time quantitative PCR machine (ABI prism 7700 sequence detection system) to perform a reaction for quantifying the gene expression levels. The reaction conditions were set as follows: i) 50° C. for 2 minutes, one cycle; ii) 95° C. for 10 minutes, one cycle; iii) 95° C. for 15 seconds, 60° C. for 30 seconds, and 72° C. for 30 seconds, repeated for 40 cycles; iv) 72° C. for 10 minutes, one cycle; and v) cooling to 4° C. to stop the reaction. The results are shown in FIGS. 5A to 5C.

Figure 5A:
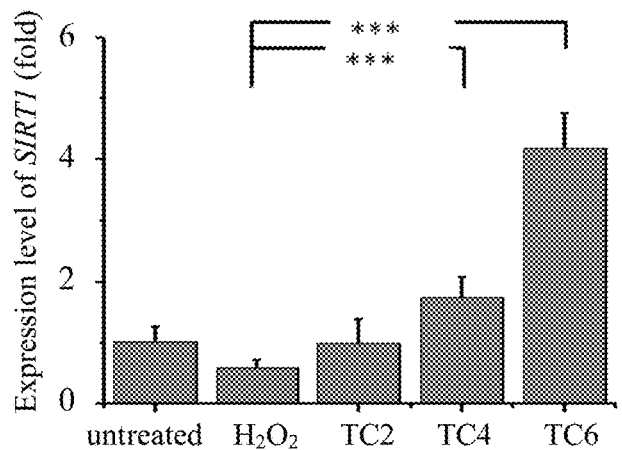
FIG. 5A is a statistical bar diagram of the results of quantitative RT-PCR, showing the expression levels of SIRT1 (silent mating type information regulation 2 homolog) gene in ADSCs without any treatment (untreated group), ADSCs treated with 2 μM of TC (TC2 group), ADSCs treated with 4 μM of TC (TC4 group) and ADSCs treated with 6 μM of TC (TC6 group), wherein the vertical axis represents the folds of the expression level of SIRT1 gene (*** represents p value<0.01, reflecting a statistically significant difference)

As shown in FIG. 5A, as compared to "$H_2O_2$ group," the expression levels of SIRT1 gene of "TC2 group," "TC4 group" and "TC6 group" were significantly increased along with the increment in the concentration of TC. These results again suggest that TC is effective in rejuvenating stem cells.

Figure 5B:
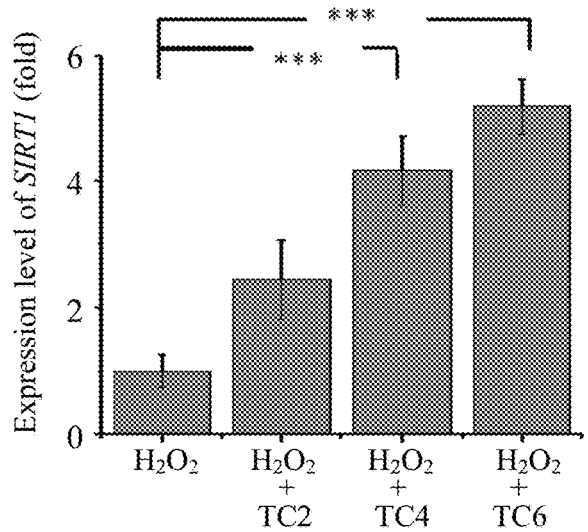
FIG. 5B is a statistical bar diagram of the results of quantitative RT-PCR, showing the expression levels of SIRT1 gene in ADSCs which have been treated with H$_2$O$_2$ to induce senescence, and then treated with 0 μM of TC (H$_2$O$_2$ group), 2 μM of TC (H$_2$O$_2$+TC2 group), 4 μM of TC (H$_2$O$_2$+TC4 group) or 6 μM of TC (H$_2$O$_2$+TC6 group), wherein the vertical axis represents the folds of the expression level of SIRT1 gene (*** represents p value<0.01, reflecting a statistically significant difference)

As shown in FIG. 5B, as compared to "$H_2O_2$ group," the expression levels of the SIRT1 gene of "$H_2O_2$+TC2 group," "$H_2O_2$+TC4 group" and "$H_2O_2$+TC6 group" were significantly increased along with the increment in the concentration of TC. These results again suggest that TC is effective in the anti-senescence of stem cells.

Figure 5C:
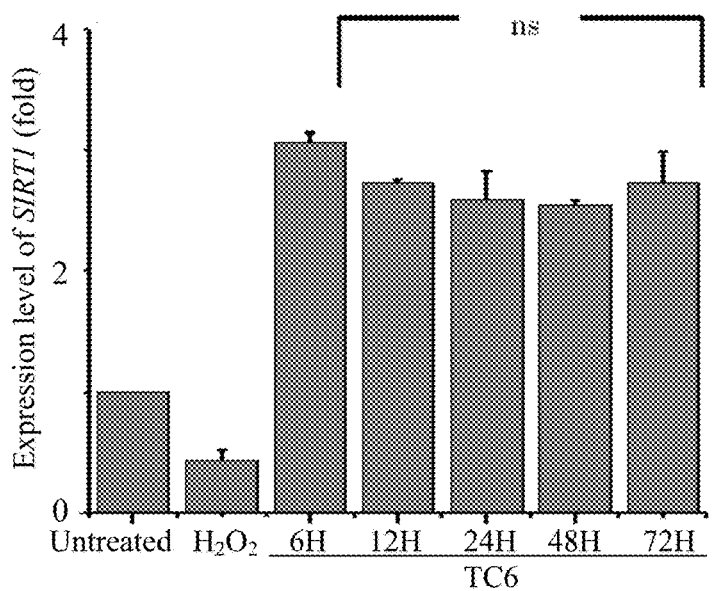
FIG. 5C is a statistical bar diagram of the results of quantitative RT-PCR, showing the expression levels of SIRT1 gene in ADSCs without any treatment (untreated group), ADSCs treated with H$_2$O$_2$ (H$_2$O$_2$ group), ADSCs treated with H$_2$O$_2$ and then treated with TC for 6 hours (TC6H group), ADSCs treated with H$_2$O$_2$ and then treated with TC for 12 hours (TC12H group), ADSCs treated with H$_2$O$_2$ and then treated with TC for 24 hours (TC24H group) and ADSCs treated with H$_2$O$_2$ and then treated with TC for 48 hours (TC48H group), wherein the vertical axis represents the folds of the expression level of SIRT1 gene (ns represents p value=0.417, reflecting no statistically significant difference)

As shown in FIG. 5C, as compared to "TC6H group," the expression levels of the SIRT1 gene of "TC12H group," "TC24H group," "TC48H group" and "TC72H group" did not show significant difference. These results indicate that the effect of TC on increasing the expression level of SIRT1 gene can be maintained for at least 72 hours.

(3-3) Semiquantitative RT-PCR

Each of the cDNA of the ADSCs of "untreated group," "$H_2O_2$ group" and "$H_2O_2$+TC6 group" from Experiment (3-1) was handled as follows. 2.5 μl the cDNA of the ADSCs was mixed with 2.5 μl of forward primer (10 μM) and 2.5 μl of reverse primer (10 μM) of SIRT1 gene, p53 gene, p21 gene, OCT4 gene, NANOG gene, TWIST1 gene or β-Actin gene as shown in Table 1, 7.5 μl of deionized water, and 12.5 μl of EconoTaq® PLUS GREEN 2× Master Mix (Lucigen, Middleton, Wis., USA). The mixture was then placed in a revers transcription polymerase chain reaction (RT-PCR) machine. The RT-PCR reaction conditions were set as follows: i) 94° C. for 30 seconds, 55° C. for 30 seconds, and 94° C. for 60 seconds, repeated for 30 cycles; ii) 72° C. for 10 minutes; and iii) cooling to 4° C. to stop the reaction. The RT-PCR product was analyzed by 2% agarose gel electrophoresis at a voltage of 100 volts for 30 minutes. Then, the gel was stained with ethidium bromide (EtBr) for 10 minutes, and photographed by a gel image documentation system (DOC PRINT DP-001FDC, VilberLourmat France).

Figure 6A:
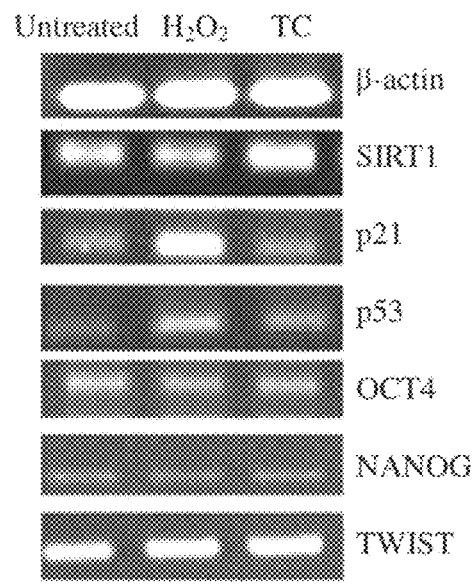
FIGS. 6A and 6B are a picture and a statistical bar diagram of semiquantitative RT-PCR, showing the expression levels of senescence-associated genes, cell cycle regulation-associated genes, and pluripotency-associated genes in ADSCs without any treatment (untreated group), ADSCs treated with H$_2$O$_2$ (H$_2$O$_2$ group) and ADSCs treated with H$_2$O$_2$ and 6 μM of TC (H$_2$O$_2$+TC6 group) respectively, wherein the vertical axis of the statistical bar diagram represents the folds of the gene expression levels.

The results are shown in FIG. 6A. The expression levels of the genes were quantified by a software, Image J. The results are shown in Table 6B.

Figure 6B:
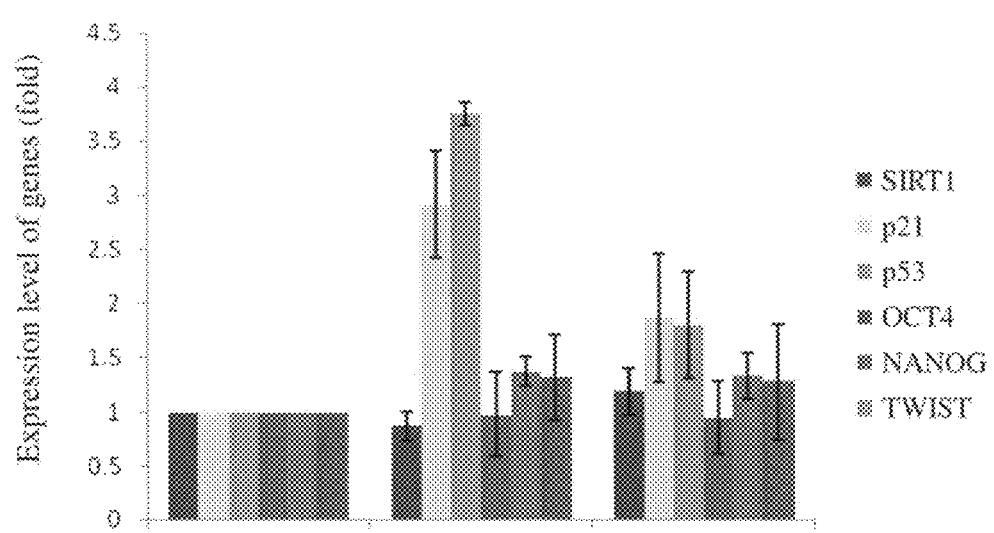

As shown in FIGS. 6A and 6B, as compared to "untreated group," the expression level of the SIRT1 gene of "$H_2O_2$ group" was significantly decreased; and as compared to "$H_2O_2$ group," the expression level of the SIRT1 gene of "$H_2O_2$+TC6 group" was significantly increased. As compared to "untreated group," the expression levels of the p21 gene and p53 gene of "$H_2O_2$ group" were significantly increased; and as compared to "$H_2O_2$ group," the expression levels of the p21 gene and p53 gene of "$H_2O_2$+TC6 group" were significantly decreased. As compared to "$H_2O_2$ group," the expression levels of the OCT4 (octamer-binding transcription factor 4) gene and NANOG gene of "$H_2O_2$+TC6 group" did not show significant difference.

It has been known that the expression level of SIRT1 gene is associated with senescence, the expression levels of p21 gene and p53 gene are associated with the regulation of cell cycle, and the expression levels of OCT4 gene and NANOG gene are associated with the pluripotency of stem cells. Accordingly, the above results indicate that TC is effective in the anti-senescence of stem cells and in regulating cell cycle, and does not affect the pluripotency of stem cells.

TABLE 1

| Gene name | Nucleotide sequence of the primers | SEQ ID NO. |
|---|---|---|
| SIRT1 | Forward: 5'-GGTGTTAAATACCAAACTGC-3' | 1 |
| | Reverse: 5'-AGGAGTGATGTTCAAAATG-3' | 2 |
| P53 | Forward: 5'-TAACAGTTCCTGCATGGGCGGC-3' | 3 |
| | Reverse: 5'-AGGACAGGCACAAACACGCACC-3' | 4 |
| p21 | Forward: 5'-CACTCCAAACGCCGGCTGATCTTC-3' | 5 |
| | Reverse: 5'-TGTAGAGCGGGCCTTTGAGGCCCTC-3' | 6 |
| OCT4 | Forward: 5'-CTTGCTGCAGAAGTGGGTGGAGGAA-3' | 7 |
| | Reverse: 5'-CTGCAGTGTGGGTTTCGGGCA-3' | 8 |
| NANOG | Forward: 5'-TGCTATTCTTCGGCCAGTTG-3' | 9 |
| | Reverse: 5'-TGCCTCACACGGAGACTGTC-3' | 10 |
| TWIST1 | Forward: 5'-GGGAGTCCGCAGTCTACGA-3' | 11 |
| | Reverse: 5'-AGACCGAGAAGGGCGTAGCTG-3' | 12 |
| β-Actin | Forward: 5'-CGCCAACCGCGAGAAGATA-3' | 13 |
| | Reverse: 5'-CGTCCCGGAGTCCATC-3' | 14 |

(3-4) Microarray Analysis

Each of the total cellular RNA of ADSCs of "$H_2O_2$ group" and "$H_2O_2$+TC6 group" from Experiment (3-1) was handled as follows. The total cellular RNA of ADSCs was reverse transcribed for about 20 or 30 amplification cycles by using a RT Pre Mix kit (purchased from iNtRON Biotechnology) and the primers of each gene as shown in Table 2, as well as the primers of SIRT1 gene or p53 gene as shown in Table 1. The products thus obtained are single strand cDNA of these genes.

The cDNA was hybridized with a gene chip (Affymetrix GeneChip Human Genome U133 plus 2.0 Array, Affymetrix). Then, the gene chip was scanned and analyzed with a microarray scanner system (Gene Chip® Scanner 3000). Table 3 shows the folds of the expression levels of the genes of "$H_2O_2$+TC6 group" as compared to that of "$H_2O_2$ group" (i.e., the gene expression level of the "$H_2O_2$ group" was set as one fold).

TABLE 2

| Gene name | Nucleotide sequence of the primers | SEQ ID NO. |
|---|---|---|
| NYFA | Forward: 5'-ATCCCAGCAGCCAGTTTGGCAG-3 | 15 |
| | Reverse: 5'-GAAAAATCGTCCTTCACCACG-3' | 16 |
| CCND1 | Forward: 5'-CTGGCCATGAACTACCTGGA-3' | 17 |
| | Reverse: 5'-GTCACACTTGATCACTCTGG-3' | 18 |
| EIF5 | Forward: 5'-TGCCCACTAGGAGAAAGGTG-3' | 19 |
| | Reverse: 5'-CGGACTCACCTCTGGAATGT-3' | 20 |
| E2F6 | Forward: 5'-ACTGGGTGTTCGGAAGAGGCGA-3' | 21 |
| | Reverse: 5'-GGGGTGCGGCCCCAAAGTT-3' | 22 |
| POLR3H | Forward: 5'-CATTTTCGCTGCGTGGTGTTTCATCC-3' | 23 |
| | Reverse: 5'-AACTTGGCTGGCTGCTGCAGTG-3' | 24 |
| hTERT | Forward: 5'-GGAGCAAGTTGCAAAGCATTG-3' | 25 |
| | Reverse: 5'-TCCCACGACGTAGTCCATGTT-3' | 26 |
| PCNA | Forward: 5'-GCCGAGATCTCAGCCATATT-3' | 27 |
| | Reverse: 5'-ATGTACTTAGAGGTACAAAT-3' | 28 |
| GADD45B | Forward: 5'-TGACAACGACATCAACATC-3' | 29 |
| | Reverse: 5'-GTGACCAGAGACAATGCAG-3 | 30 |
| PIM1 | Forward: 5'-GGCGCCGGGCAAAGAGAAGGAG-3' | 31 |
| | Reverse: 5'-ACCCGAAGTCGATGAGTTTGATTT-3' | 32 |
| p16 | Forward: 5'-CAACGCACCGAATAGTTACG-3' | 33 |
| | Reverse: 5'-CAGCTCCTCAGCCAGGTC-3' | 34 |

TABLE 3

| Gene name | Significance of the increment in the of gene expression level | Folds ($p < 0.05$) |
|---|---|---|
| NYFA | Up-regulated transcription of various genes (e.g., albumin) | 7.2 |
| CCND1 | Up-regulated proliferation of the cells | 5.8 |
| EIF5 | Up-regulated translation | 3.4 |
| SIRT1 | Up-regulated activity of telomerase | 2.4 |
| E2F6 | The increment of proliferation of cells | 2.2 |
| POLR3H | Up-regulated transcriptional activity | 2.2 |
| hTERT | Up-regulated activity of telomerase | 2 |
| PCNA | The increment of proliferation of the cells | 2 |
| GADD45B | Apoptosis | −4.6 |
| PIM1 | The increment of cytokine and the activation of pro-apoptotic genes | −4.4 |
| p53 | Increased apoptosis | −1 |
| p16 | Increased senescence of the cells | −1.8 |

As shown in Table 3, as compared to the "$H_2O_2$ group" ADSCs, the "$H_2O_2$+TC6 group" ADSCs were significantly increased in the expression levels of the proliferation-associated genes (e.g., NYFA, CCND1, EIF5, SIRT1, E2F6, POLR3H, hTERT and PCNA) but significantly decreased in the expression levels of apoptosis-associated genes (e.g., GADD45B, PIM1, p53 and p16). The aforementioned results indicate that TC is effective in improving cell proliferation rate by increasing the expression levels of the transcription-associated genes, translation-associated genes, and SIRT1 gene in the cells.

Experiment (4) Telomerase Activity Assay

It has been know that the activity of telomerase plays a key role in controlling cell senescence. The activity of telomerase in each of the "untreated group," "$H_2O_2$ group" and "TC6 group" ADSCs from Example 1 (1) was analyzed by Telomeric Repeat Amplification Protocol (TRAP) as follows. The 3'-end primer of telomere (i.e., Telo TAGGG) was extended by PCR under the catalysis of telomerase to amplify the TTAGGG repeat sequence. Then, signals of the product were detected by enzyme-linked immunosorbent assay (ELISA). The results are shown in FIG. 7, wherein the activity of telomerase in HEK293 cells (without any treatment) was served as a positive control group.

Figure 7:
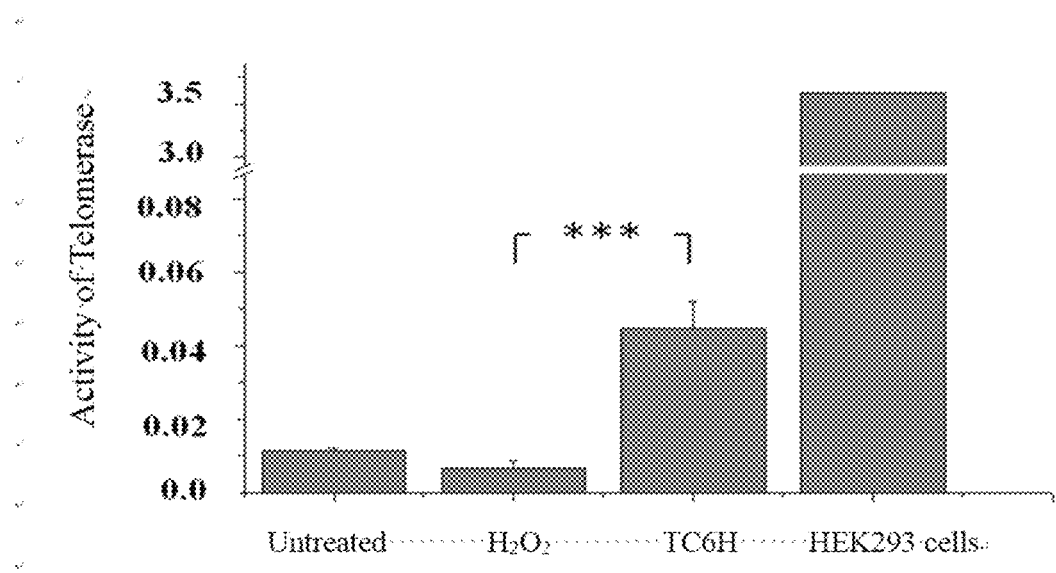
FIG. 7 is a statistical bar diagram showing the activity of telomerase in ADSCs without any treatment (untreated group), ADSCs treated with H$_2$O$_2$ (H$_2$O$_2$ group), ADSCs treated with H$_2$O$_2$ and 6 μM of TC (H$_2$O$_2$+TC6 group) and HEK293 cells, wherein the vertical axis represents the activity of telomerase (*** represents p value<0.01, reflecting a statistically significant difference)

As shown in FIG. 7, as compared to "untreated group," the activity of the telomerase of "$H_2O_2$ group" was significantly decreased; and as compared to "$H_2O_2$ group," the activity of telomerase of "TC6 group" was significantly increased. The aforementioned results indicate that the $H_2O_2$ treatment would lead to the senescence of stem cells, and the activity of the telomerase in the senescent stem cells could be increased by TC treatment. These results again suggest that TC is effective in the anti-senescence of stem cells.

Experiment (5) Tests of BMMSCs and WJSCs (5-1) SA-β-Gal Activity Assay

The steps shown in Experiment (2) of Example 4 were repeated, but the ADSCs were substituted with the BMMSCs or WJSCs from Example 1. The results are shown in FIGS. 8A to 8D and 9A to 9D.

As shown in FIGS. 8A to 8D, as compared to the "untreated group" hBMMSCs, the number of the SA-β-gal activity-positive hBMMSCs in the "$H_2O_2$ group" was significantly increased. As compared to the "$H_2O_2$ group" hBMMSCs, the number of the SA-β-gal activity-positive hBMMSCs in the "$H_2O_2$+TC6 group" were significantly reduced. The aforementioned results were in line with those of ADSCs.

As shown in FIGS. 9A to 9D, as compared to the "untreated group" WJSCs, the number of the SA-β-gal activity-positive WJSCs in the "$H_2O_2$ group" was significantly increased. As compared to the "$H_2O_2$ group" WJSCs, the number of the SA-β-gal activity-positive WJSCs in the "$H_2O_2$+TC6 group" were significantly reduced. Again, the aforementioned results were in line with those of ADSCs.

(5-2) Analysis of the Expression Level of SIRT1 Gene

The steps as shown in Experiment (3-2) were repeated, but the cDNA was substituted with the cDNA of the BMMSCs or WJSCs from Experiment (3-1) to conduct quantitative RT-PCR. The results are shown in FIGS. 10A and 10B.

Figure 10A:
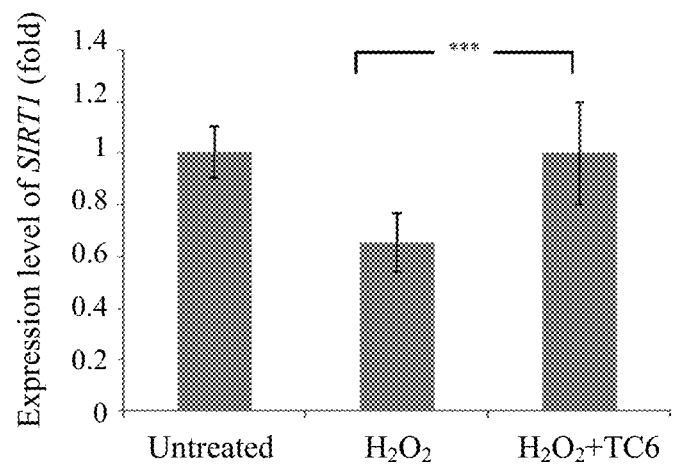
FIG. 10A is a statistical bar diagram of the results of quantitative RT-PCR, showing the expression levels of SIRT1 gene in hBMMSCs without any treatment (untreated group), hBMMSCs treated with H$_2$O$_2$ (H$_2$O$_2$ group) and hBMMSCs treated with H$_2$O$_2$ and 6 μM of TC (H$_2$O$_2$+TC6 group), wherein the vertical axis represents the expression folds of SIRT1 gene (*** represents p value<0.05, reflecting a statistically significant difference)

As shown in FIG. 10A, as compared to the "untreated group" hBMMSCs, the expression level of SIRT1 gene in the "$H_2O_2$ group" hBMMSCs was significantly reduced. This result suggests that $H_2O_2$ would lead to the senescence of stem cells. As compared to the "$H_2O_2$ group" hBMMSCs, the expression level of SIRT1 gene in the "$H_2O_2$+TC6 group" hBMMSCs was significantly increased. This result suggests that TC is effective in the anti-senescence of stem cells. The aforementioned results were in line with those of ADSCs.

Figure 10B:
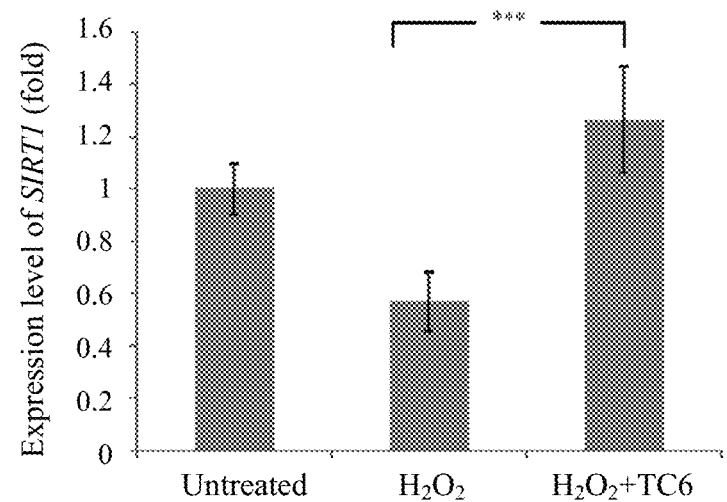
FIG. 10B is a statistical bar diagram of the results of quantitative RT-PCR, showing the expression levels of SIRT1 gene in WJSCs without any treatment (untreated group), WJSCs treated with H$_2$O$_2$ (H$_2$O$_2$ group) and WJSCs treated with H$_2$O$_2$ and 6 μM of TC (H$_2$O$_2$+TC6 group), wherein the vertical axis represents the expression folds of SIRT1 gene (*** represents p value<0.05, reflecting a statistically significant difference)

As shown in FIG. 10B, as compared to the "untreated group" WJSCs, the expression level of SIRT1 gene in the "$H_2O_2$ group" WJSCs was significantly reduced. This result suggests that $H_2O_2$ would lead to the senescence of stem cells. As compared to the "$H_2O_2$ group" WJSCs, the expression level of SIRT1 gene in the "$H_2O_2$+TC6 group" WJSCs was significantly increased. This result suggests that TC is effective in the anti-senescence of stem cells. Again, the aforementioned results were in line with those of ADSCs.

B. Animal Experiments

[Example 5] Establishment of a Liver Fibrosis Rat Model 200 mg/kg of thioacetamide (TAA) was intraperitoneally injected to 8-week-old male Wister rats (n=35) once every three days for 60 days (i.e., 20 injections in total) to obtain a liver fibrosis rat model (hereinafter referred to as the "TAA group" rat). Additionally, rats that injected with equal volume of normal saline but not TAA were served as a "control group" (n=12). At 4 days after the last injection, four rats in the "control group" and three rats in the "TAA group" were anesthetized with ether and analyzed by the following experiments.

Experiment (1) Evaluation of Histopathological Score

The liver tissue of the "control group" and "TAA group" rats were processed, biopsied, sliced and stained to evaluate the histopathological score. The results are shown in FIGS. 11A and 11B. The staining methods include Hematoxylin and Eosin staining (H&E staining) and Masson's trichrome staining. The steps of the staining can be seen in "Adipose-derived stem cells can abrogate chemical-induced liver fibrosis and facilitate recovery of liver function. Cell Transplant. 21(12):2753-2764 (2012)," which is entirely incorporated hereinto by reference. The results of H&E staining and Masson's trichrome staining were analyzed by a Metavir scoring system to obtain activity score and fibrosis score as shown in Table 4. A higher activity score indicates severer liver inflammation, and a higher fibrosis score indicates a more severe liver fibrosis.

TABLE 4

| Fibrosis score | Definition | Activity score | Definition |
|---|---|---|---|
| F0 | No fibrosis | 0 | No inflammation |
| F1 | Portal fibrosis without septa | 1 | Mild inflammation |
| F2 | Portal fibrosis with few septa | 2 | Moderate inflammation |
| F3 | Numerous septa | 3 | Severe inflammation |
| F4 | Cirrhosis | | |

As shown in FIG. 11A (showing the results of the Masson's trichrome staining), collagen accumulated in the liver tissue of the "TAA group" rats and connected two blood vessels, which is a phenomenon of liver fibrosis. The results of FIG. 11A were further analyzed by the Metavir scoring system. As compared to the fibrosis score of the "control group" rats (i.e., 0), the fibrosis score of the "TAA group" rats is 4. The aforementioned results indicate that long-term TAA injection would lead to severe liver fibrosis (even liver cirrhosis) of a rat.

As shown in FIG. 11B (showing the results of the H&E staining), the liver tissue of the "TAA group" rats was significantly infiltrated by macrophages. The results of FIG. 11B were further analyzed by the Metavir scoring system. As compared to the activity score of the "control group" rats (i.e., 0), the activity score of the "TAA group" rats is 3. The aforementioned results indicate that long-term TAA injection would lead to severe inflammation in the liver of a rat.

Experiment (2) Analysis of Biochemical Functional Indexes

The cardiac blood of the "control group" and "TAA group" rats was collected and measured by a biochemical analyzer (Roche, Integra 800) to analyze the biochemical functional indexes, and thereby, evaluating the extent of hepatic damage. The biochemical functional indexes include the expression level of glutamate oxaloacetate transaminase (GOT), the expression level of glutamate pyruvate transaminase (GPT), the expression level of albumin, the expression level of total bilirubin, and prothrombin time. The results are shown in Table 5.

TABLE 5

|  | "Control group" rats (n = 6) | "TAA group" rats (n = 3) |
|---|---|---|
| GOT (Units/L) | 91 ± 32 | 546 ± 48** |
| GPT (Units/L) | 42 ± 12 | 138 ± 47** |
| Albumin (g/dL) | 3.9 ± 0.3 | 2.8 ± 0.4** |
| Prothrombin time (sec) | 10.78 ± 0.26 | 16.4 ± 3.0** |
| Total bilirubin (mg/dL) | 0.025 ± 0.05 | 0.049 ± 0.009** |
| Activity score | 0 | 3.03 ± 0.05*** |
| Fibrosis score | 0 | 4 ± 0.2*** |

As shown in Table 5, as compared to the "control group" rats, the expression levels of GOT, GPT and total bilirubin in the blood and the prothrombin time of the "TAA group" rats were significantly increased, and the expression level of albumin in the blood of the "TAA group" rats was significantly reduced. The results confirm that long-term TAA injection would lead to severe damage in the liver of a rat.

[Example 6] The Effects of TC on Enhancing the Therapeutic Effect of Stem Cells

The remaining 32 "TAA group" rats from Example 5 were divided into "pseudo-injection group," "stem cell group," "$H_2O_2$ group" and "TC group," each group had 8 rats and treated with different conditions, wherein the day for performing the treatment was referred to as "Day 0" post treatment. The liver of the "pseudo-injection group" rats were injected with 300 μl of normal saline. The livers of "stem cell group" rats (i.e., positive control group) were injected with 300 μl of the "untreated group" ADSCs (contains $1 \times 10^6$ cells) obtained from Example 1. The livers of the "$H_2O_2$ group" rats (i.e., negative control group) were injected with 300 μl of the "$H_2O_2$ group" ADSCs (contains $1 \times 10^6$ cells) obtained from Example 1. The livers of the "TC group" rats were injected with 300 μl of the "$H_2O_2$+TC6 group" ADSCs (contains $1 \times 10^6$ cells) obtained from Example 1.

Four rats from each group were sacrificed with ether at "Day 7" post the different treatments. Then, the other four rats from each group were sacrificed at "Day 14" post the treatments. The cardiac blood samples and liver tissue samples of each group were collected, and analyzed as follows.

Experiment (1) α-Fetoprotein (AFP) Immunohistostaining

The liver tissue sections of the "control group," "pseudo-injection group," "stem cell group," "$H_2O_2$ group" and "TC group" were analyzed by AFP immunohistostaining using an α-fetoprotein (AFP) antibody (purchased from Calbiochem, ST1673). The results of "Day 7" post the stem cells injection are shown in FIGS. 12A to 12E, and the results of "Day 14" post the stem cell injection are shown in FIGS. 12F to 12J. Since the AFP antibody is specific to human AFP, the AFP signal-positive cells (i.e., the brown cells indicated by arrows shown in the Figures) represent cells originated from the injected ADSCs which can differentiate into hepatocyte-like cells.

As shown in FIGS. 12A to 12J, the liver tissues of the "stem cell group," "$H_2O_2$ group" and "TC group" at "Day 7" and "Day 14" post the stem cell injection showed numerous AFP signal-positive cells (i.e., the cells indicated by the arrows shown in the Figures). These results indicate that all of the stem cells in each group can survive and differentiate after being injected into the liver of the rats. The therapeutic effects of the stem cells in each group on the liver fibrosis rats were observed in the following experiments.

Experiment (2) Evaluation of Histopathological Score

Figure 14A:
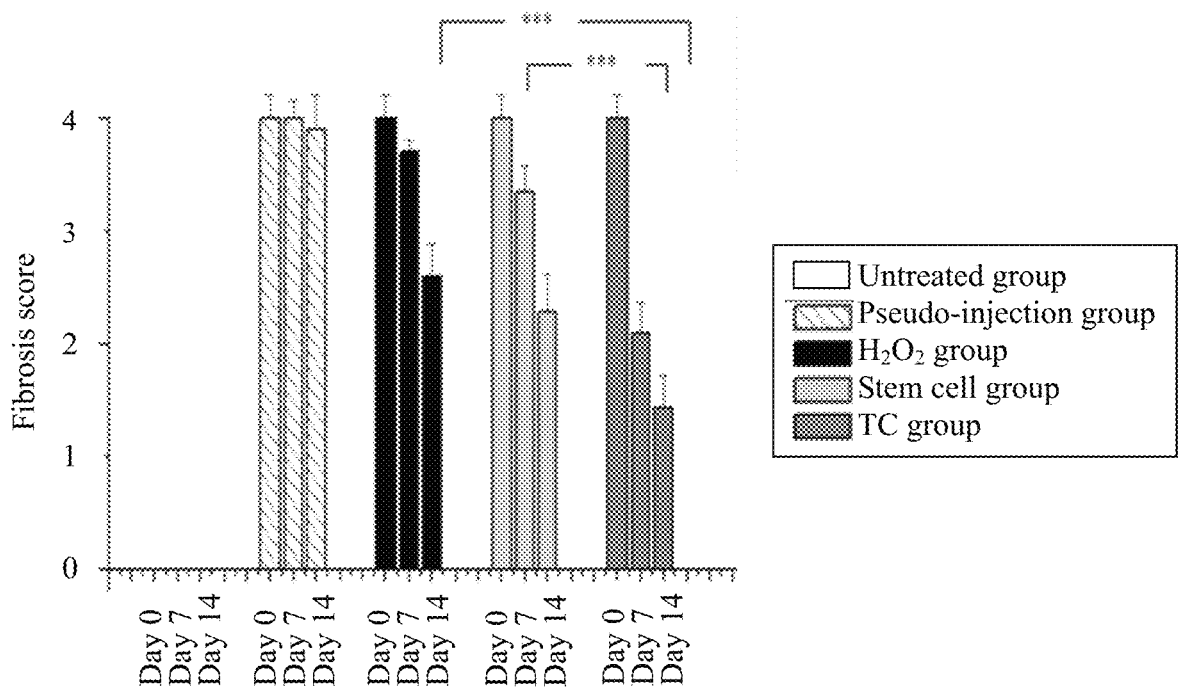
FIGS. 14A and 14B are statistical bar diagrams showing the fibrosis score and activity score of rats at Day 0, Day 7 and Day 14 post the different treatments, wherein ▢ represents the rats without any treatment (untreated group), ▨ represents the rats injected with normal saline (pseudo-injection group), ■ represents the rats injected with "$H_2O_2$ group" ADSCs ($H_2O_2$ group), ▩ represents the rats injected with "untreated group" ADSCs (stem cell group), and ▩ represents the rats injected with "$H_2O_2$+TC6 group" ADSCs (TC group)
Figure 14B:
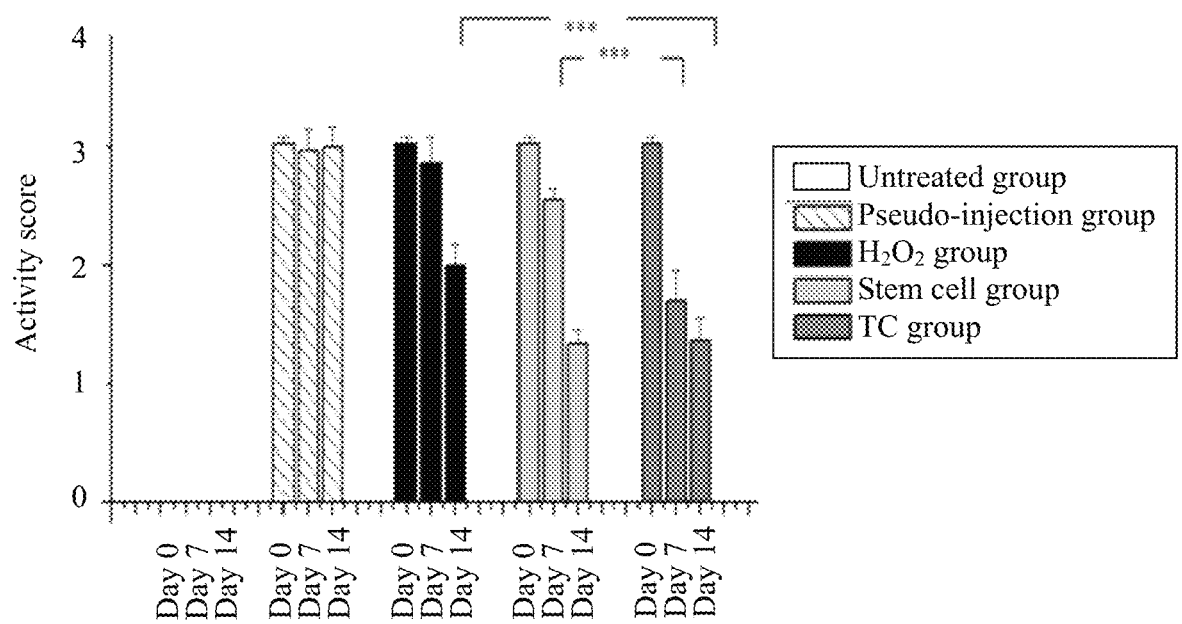

The histopathological score of the cardiac blood samples of the "control group," "pseudo-injection group," "stem cell group," "$H_2O_2$ group" and "TC group" were evaluated by the steps as shown in Example 5 (1). The results are shown in FIGS. 13A to 13D, 14A and 14B, wherein the results of the Masson's trichrome staining are shown in FIGS. 13A and 13B, and the results of the H&E staining are shown in FIGS. 13C and 13D. In addition, the results of FIGS. 14A and 14B are digitized and shown in Table 6.

TABLE 6

|  | Fibrosis score | Activity score |
|---|---|---|
| Control group | 0 | 0 |
| Pseudo-injection group | 4 | 3 |
| $H_2O_2$ group | 3 to 4 | 2 to 3 |
| Stem cell group | 2 to 3 | 1 to 2 |
| TC group | 1 to 2 | 1 to 2 |

As shown in FIGS. 13A to 13D, 14A and 14B and Table 6, long-term TAA injection may lead to severe inflammation in the rat liver, wherein the liver tissue was infiltrated by macrophages and thus cause severe liver fibrosis (even liver cirrhosis). The treatment of "$H_2O_2$+TC6 group" ADSCs is effective in reducing the inflammation of fibrosis rat liver and alleviating the degree of fibrosis.

Experiment (3) Analysis of Biochemical Functional Indexes

The biochemical functional indexes of cardiac blood samples of the "control group," "pseudo-injection group," "stem cell group," "$H_2O_2$ group" and "TC group" were analyzed by the steps as shown in Example 5 (2). The results are shown in FIGS. 15A to 15E.

Figure 15A:
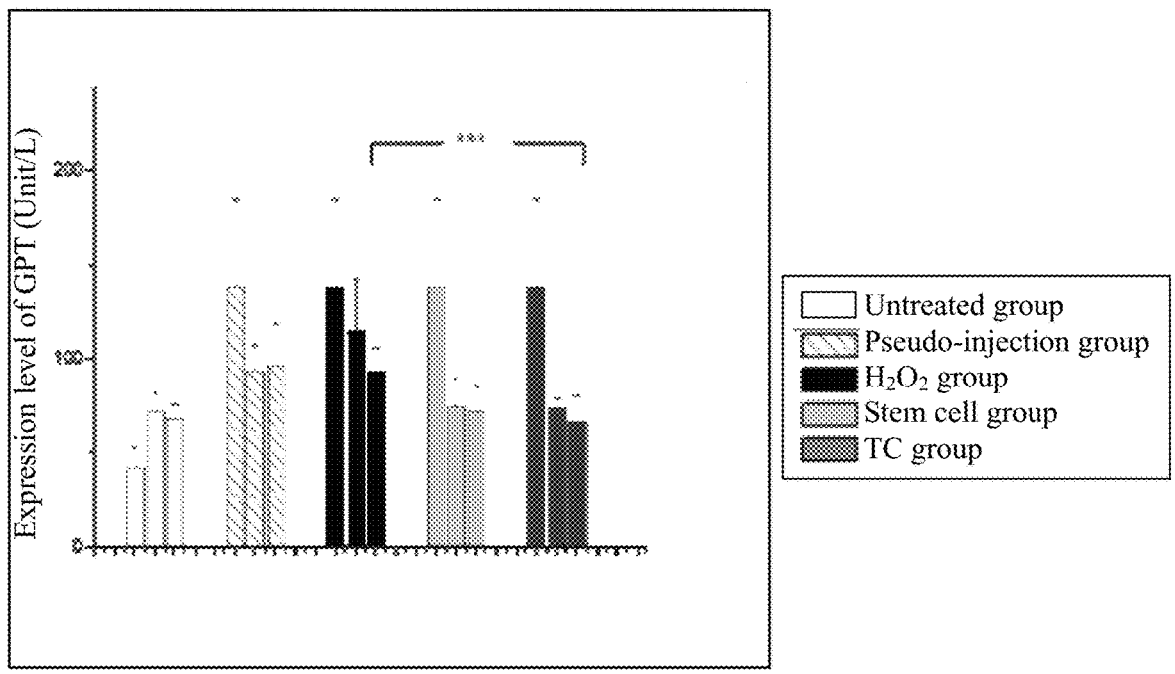
FIGS. 15A to 15E are statistical bar diagrams showing the expression level of GPT, the expression level of GOT, the expression level of albumin, prothrombin time, and the expression level of total bilirubin respectively in the livers of the rats at Day 0, Day 7 and Day 14 post the different treatments, wherein ▢ represents the rats without any treatment (untreated group), ▨ represents the rats injected with normal saline (pseudo-injection group), ■ represents the rats injected with "$H_2O_2$ group" ADSCs ($H_2O_2$ group), ▩ represents the rats injected with "untreated group" ADSCs (stem cell group), and ▩ represents the rats injected with "$H_2O_2$+TC6 group" ADSCs (TC group) (* represents p value<0.01, reflecting a statistically significant difference;  represents p value <0.05, reflecting a statistically significant difference).

As shown in FIG. 15A, at "Day 14" post the treatment, as compared to the expression level of GPT of the "$H_2O_2$ group" (i.e., 93±13 Units/L), the expression level of GPT of the "stem cell group" (i.e., 72±14 Units/L) was significantly reduced. As compared to the "stem cell group," the expression level of GPT of the "TC group" (i.e., 66±14 Units/L) was also significantly reduced. These results indicate that the treatment of the "$H_2O_2$+TC6 group" ADSCs is effective in reducing the expression level of GPT in the blood of rats with liver fibrosis.

Figure 15B:
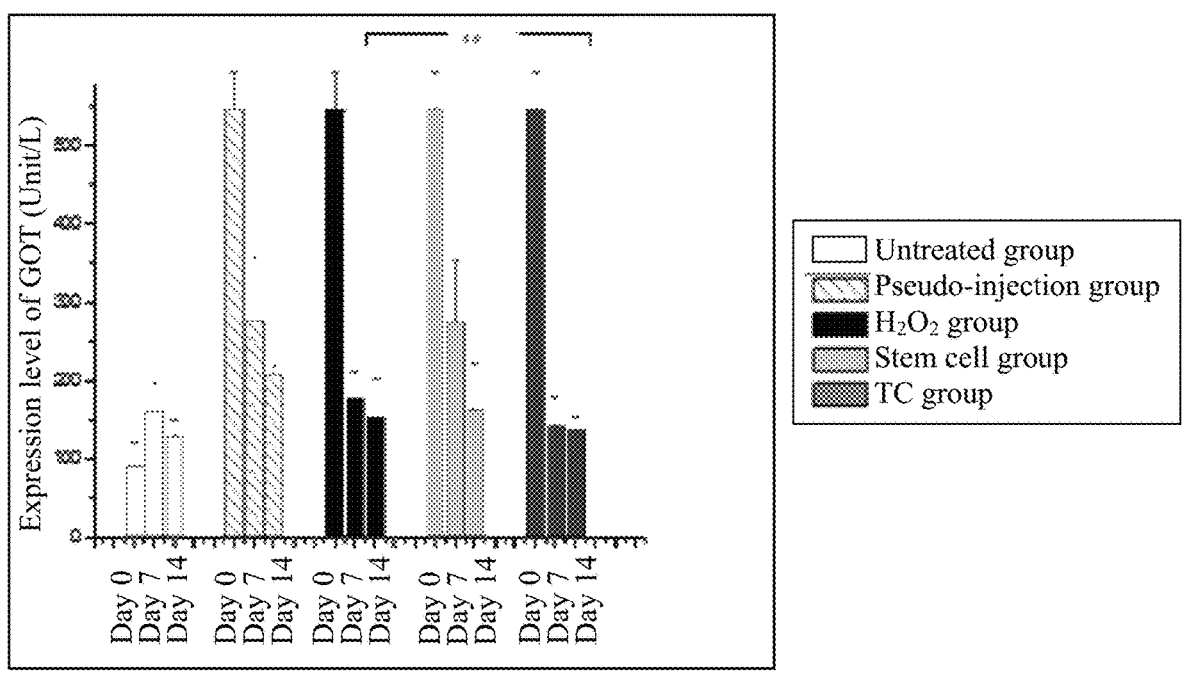

As shown in FIG. 15B, at "Day 14" post the treatment, as compared to the expression level of GOT of the "pseudo-injection group" (i.e., 208±12 Units/L), the expression level of GOT of the "stem cell group" (i.e., 162±60 Units/L) was significantly reduced. As compared to the "stem cell group," the expression level of GOT of the "TC group" (i.e., 137±18

Units/L) was also significantly reduced. These results indicate that the treatment of the "$H_2O_2$+TC6 group" ADSCs is effective in reducing the expression level of GOT in the blood of rats with liver fibrosis.

Figure 15C:
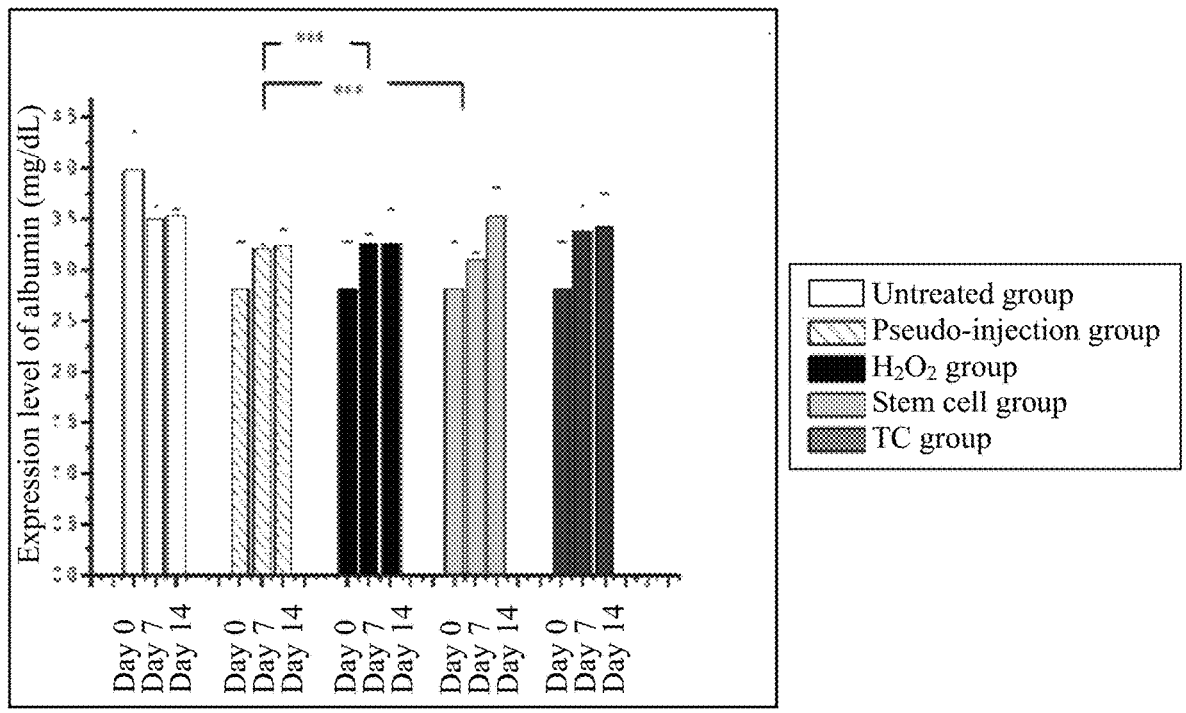

As shown in FIG. 15C, at "Day 14" post the treatment, as compared to the expression level of albumin of the "stem cell group" (i.e., 3.52±0.28 g/dL), the expression level of albumin of the "pseudo-injection group" (i.e., 3.23±0.01 g/dL) was significantly reduced. As compared to the "pseudo-injection group," the expression level of albumin of the "TC group" (i.e., 3.48±0.03 g/dL) was significantly increased. These results indicate that the treatment of the "$H_2O_2$+TC6 group" ADSCs is effective in increasing the expression level of albumin in the blood of rats with liver fibrosis.

Figure 15D:
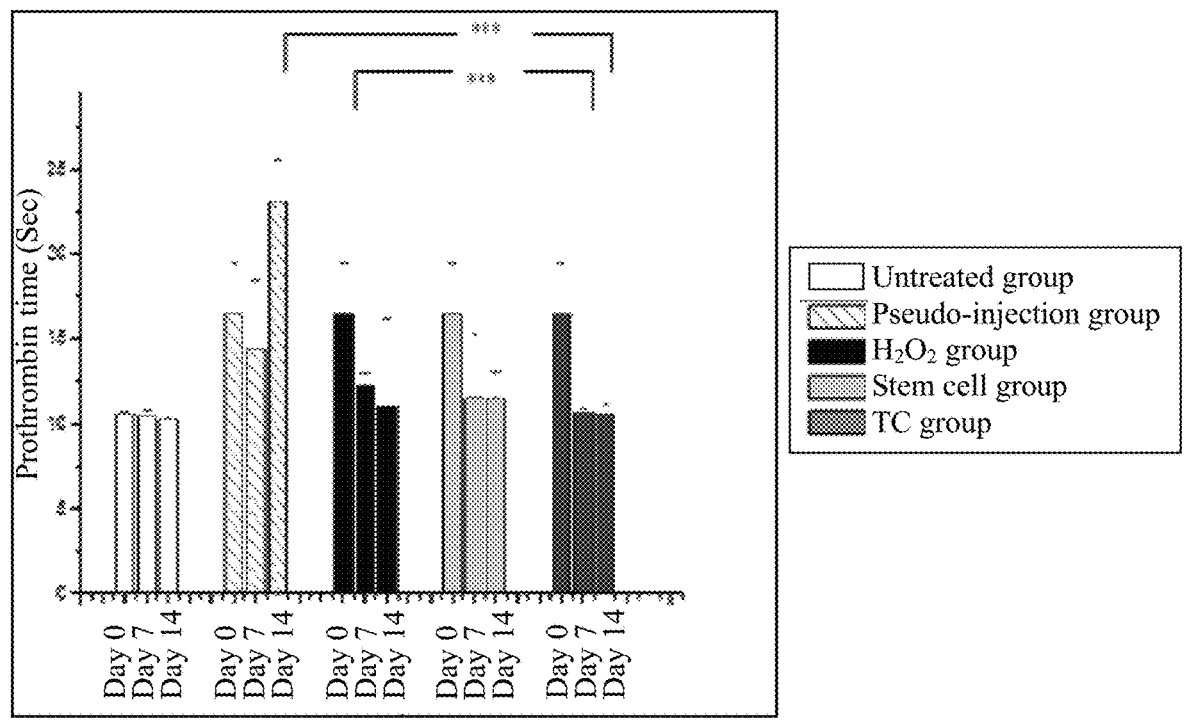

As shown in FIG. 15D, at "Day 14" post the treatment, as compared to the prothrombin time of the "pseudo-injection group" (i.e., 23.10±2.5 sec), the prothrombin time of the "TC group" (i.e., 10.88±0.67 sec) was significantly reduced. These results indicate that the treatment of the "$H_2O_2$+TC6 group" ADSCs is effective in reducing the prothrombin time in the blood of rats with liver fibrosis.

Figure 15E:
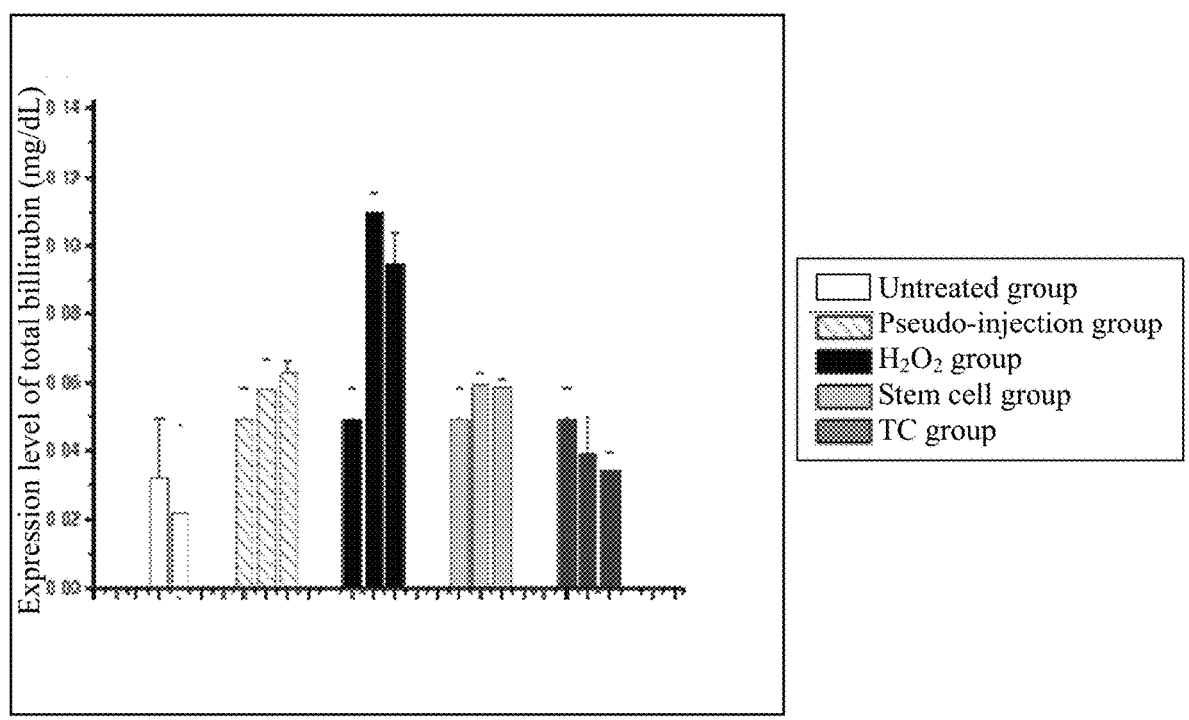

As shown in FIG. 15E, at "Day 14" post the treatment, as compared to the expression level of the total bilirubin of the "stem cell group" (i.e., 0.05±0.02 mg/dL), the expression level of the total bilirubin of the "TC group" (i.e., 0.034±0.03 mg/dL) was significantly reduced and closed to that of the "control group" (i.e., 0.02±0.02 mg/dL). These results indicate that the treatment of the "$H_2O_2$+TC6 group" ADSCs is effective in reducing the expression level of total bilirubin in the blood of rats with liver fibrosis.

The above results indicate that the treatment of TC is effective in the anti-senescence of stem cells, and thus, can enhance the therapeutic effect of the stem cells.

The above examples are used to illustrate the principle and efficacy of the present invention but not used to limit to the present invention. People skilled in this field may proceed with a variety of modifications and replacements based on the disclosures and suggestions of the invention as described without departing from the technical principle and spirit thereof. Therefore, the scope of protection of the present invention is that as defined in the claims as appended.

What is claimed is:

1. A method for the anti-senescence of a stem cell, consisting of treating the stem cell with a composition consisting of trans-cinnamaldehyde (TC) and a carrier, wherein the treatment is conducted in a culture medium of the stem cell at a TC concentration of 0.26 µg per mL of the culture medium, and wherein the carrier is selected from the group consisting of dimethyl sulfoxide (DMSO), ethanol, and 0.5% methylcellulose-containing phosphate buffered saline (PBS).

2. The method as claimed in claim 1, wherein the stem cell, is an embryonic stem cell, an adult stem cell, or an induced pluripotent stem cell.

3. The method as claimed in claim 1, wherein the stem cell is an adult stem cell.

4. The method as claimed in claim 3, wherein the adult stem cell is an adipose-derived stem cell, a bone marrow mesenchymal stem cell or a Wharton's jelly stem cell.

* * * * *

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: SIRT1 primer- Forward Sequence

<400> SEQUENCE: 1
ggtgttaaat accaaactgc                                           20

<210> SEQ ID NO 2
<211> LENGTH: 19
<212> TYPE: DNA
<213> ORGANISM: Artificial Sequence
<220> FEATURE:
<223> OTHER INFORMATION: SIRT1 primer- Reverse Sequence

<400> SEQUENCE: 2
aggagtgatg ttcaaaatg                                            19

<210> SEQ ID NO 3
<211> LENGTH: 22
<212> TYPE: DNA
<213> ORGANISM: Artificial Sequence
<220> FEATURE:
<223> OTHER INFORMATION: p53 primer- Forward Sequence

<400> SEQUENCE: 3
taacagttcc tgcatgggcg gc                                        22

<210> SEQ ID NO 4
<211> LENGTH: 22
<212> TYPE: DNA
<213> ORGANISM: Artificial Sequence
<220> FEATURE:
<223> OTHER INFORMATION: p5 primer- Reverse Sequence

<400> SEQUENCE: 4
aggacaggca caaacacgca cc                                        22
```

```
<210> SEQ ID NO 5
<211> LENGTH: 24
<212> TYPE: DNA
<213> ORGANISM: Artificial Sequence
<220> FEATURE:
<223> OTHER INFORMATION: p21 primer- Forward Sequence

<400> SEQUENCE: 5
cactccaaac gccggctgat cttc                                           24

<210> SEQ ID NO 6
<211> LENGTH: 25
<212> TYPE: DNA
<213> ORGANISM: Artificial Sequence
<220> FEATURE:
<223> OTHER INFORMATION: p21 primer- Reverse Sequence

<400> SEQUENCE: 6
tgtagagcgg gcctttgagg ccctc                                          25

<210> SEQ ID NO 7
<211> LENGTH: 25
<212> TYPE: DNA
<213> ORGANISM: Artificial Sequence
<220> FEATURE:
<223> OTHER INFORMATION: OCT4 primer- Forward Sequence

<400> SEQUENCE: 7
cttgctgcag aagtgggtgg aggaa                                          25

<210> SEQ ID NO 8
<211> LENGTH: 21
<212> TYPE: DNA
<213> ORGANISM: Artificial Sequence
<220> FEATURE:
<223> OTHER INFORMATION: OCT4 primer- Reverse Sequence

<400> SEQUENCE: 8
ctgcagtgtg ggtttcgggc a                                              21

<210> SEQ ID NO 9
<211> LENGTH: 20
<212> TYPE: DNA
<213> ORGANISM: Artificial Sequence
<220> FEATURE:
<223> OTHER INFORMATION: NANOG primer- Forward Sequence

<400> SEQUENCE: 9
tgctattctt cggccagttg                                                20

<210> SEQ ID NO 10
<211> LENGTH: 20
<212> TYPE: DNA
<213> ORGANISM: Artificial Sequence
<220> FEATURE:
<223> OTHER INFORMATION: NANOG primer- Reverse Sequence

<400> SEQUENCE: 10
tgcctcacac ggagactgtc                                                20

<210> SEQ ID NO 11
<211> LENGTH: 19
<212> TYPE: DNA
<213> ORGANISM: Artificial Sequence
<220> FEATURE:
<223> OTHER INFORMATION: TWIST1 primer- Forward Sequence
```

<400> SEQUENCE: 11
gggagtccgc agtctacga                                                    19

<210> SEQ ID NO 12
<211> LENGTH: 21
<212> TYPE: DNA
<213> ORGANISM: Artificial Sequence
<220> FEATURE:
<223> OTHER INFORMATION: TWIST1 primer- Reverse Sequence

<400> SEQUENCE: 12
agaccgagaa gggcgtagct g                                                 21

<210> SEQ ID NO 13
<211> LENGTH: 19
<212> TYPE: DNA
<213> ORGANISM: Artificial Sequence
<220> FEATURE:
<223> OTHER INFORMATION: Actin primer- Forward Sequence

<400> SEQUENCE: 13
cgccaaccgc gagaagata                                                    19

<210> SEQ ID NO 14
<211> LENGTH: 16
<212> TYPE: DNA
<213> ORGANISM: Artificial Sequence
<220> FEATURE:
<223> OTHER INFORMATION: Actin primer- Reverse Sequence

<400> SEQUENCE: 14
cgtcccggag tccatc                                                       16

<210> SEQ ID NO 15
<211> LENGTH: 22
<212> TYPE: DNA
<213> ORGANISM: Artificial Sequence
<220> FEATURE:
<223> OTHER INFORMATION: NYFA primer- Forward Sequence

<400> SEQUENCE: 15
atcccagcag ccagtttggc ag                                                22

<210> SEQ ID NO 16
<211> LENGTH: 21
<212> TYPE: DNA
<213> ORGANISM: Artificial Sequence
<220> FEATURE:
<223> OTHER INFORMATION: NYFA primer- Reverse Sequence

<400> SEQUENCE: 16
gaaaaatcgt ccttcaccac g                                                 21

<210> SEQ ID NO 17
<211> LENGTH: 20
<212> TYPE: DNA
<213> ORGANISM: Artificial Sequence
<220> FEATURE:
<223> OTHER INFORMATION: CCND1 primer- Forward Sequence

<400> SEQUENCE: 17
ctggccatga actacctgga                                                   20

<210> SEQ ID NO 18
<211> LENGTH: 20

```
<212> TYPE: DNA
<213> ORGANISM: Artificial Sequence
<220> FEATURE:
<223> OTHER INFORMATION: CCND1 primer- Reverse Sequence

<400> SEQUENCE: 18
gtcacacttg atcactctgg                                              20

<210> SEQ ID NO 19
<211> LENGTH: 20
<212> TYPE: DNA
<213> ORGANISM: Artificial Sequence
<220> FEATURE:
<223> OTHER INFORMATION: EIF5 primer- Forward Sequence

<400> SEQUENCE: 19
tgcccactag gagaaaggtg                                              20

<210> SEQ ID NO 20
<211> LENGTH: 20
<212> TYPE: DNA
<213> ORGANISM: Artificial Sequence
<220> FEATURE:
<223> OTHER INFORMATION: EIF5 primer- Reverse Sequence

<400> SEQUENCE: 20
cggactcacc tctggaatgt                                              20

<210> SEQ ID NO 21
<211> LENGTH: 22
<212> TYPE: DNA
<213> ORGANISM: Artificial Sequence
<220> FEATURE:
<223> OTHER INFORMATION: E2F6 primer- Forward Sequence

<400> SEQUENCE: 21
actgggtgtt cggaagaggc ga                                           22

<210> SEQ ID NO 22
<211> LENGTH: 19
<212> TYPE: DNA
<213> ORGANISM: Artificial Sequence
<220> FEATURE:
<223> OTHER INFORMATION: E2F6 primer- Reverse Sequence

<400> SEQUENCE: 22
ggggtgcggc cccaaagtt                                               19

<210> SEQ ID NO 23
<211> LENGTH: 26
<212> TYPE: DNA
<213> ORGANISM: Artificial Sequence
<220> FEATURE:
<223> OTHER INFORMATION: PLOR3H primer- Forward Sequence

<400> SEQUENCE: 23
cattttcgct gcgtggtgtt tcatcc                                       26

<210> SEQ ID NO 24
<211> LENGTH: 22
<212> TYPE: DNA
<213> ORGANISM: Artificial Sequence
<220> FEATURE:
<223> OTHER INFORMATION: PLOR3H primer- Reverse Sequence

<400> SEQUENCE: 24
```

```
aacttggctg gctgctgcag tg                                              22

<210> SEQ ID NO 25
<211> LENGTH: 21
<212> TYPE: DNA
<213> ORGANISM: Artificial Sequence
<220> FEATURE:
<223> OTHER INFORMATION: hTERT primer- Forward Sequence

<400> SEQUENCE: 25
ggagcaagtt gcaaagcatt g                                               21

<210> SEQ ID NO 26
<211> LENGTH: 21
<212> TYPE: DNA
<213> ORGANISM: Artificial Sequence
<220> FEATURE:
<223> OTHER INFORMATION: hTERT primer- Reverse Sequence

<400> SEQUENCE: 26
tcccacgacg tagtccatgt t                                               21

<210> SEQ ID NO 27
<211> LENGTH: 20
<212> TYPE: DNA
<213> ORGANISM: Artificial Sequence
<220> FEATURE:
<223> OTHER INFORMATION: PCNA primer- Forward Sequence

<400> SEQUENCE: 27
gccgagatct cagccatatt                                                 20

<210> SEQ ID NO 28
<211> LENGTH: 20
<212> TYPE: DNA
<213> ORGANISM: Artificial Sequence
<220> FEATURE:
<223> OTHER INFORMATION: PCNA primer- Reverse Sequence

<400> SEQUENCE: 28
atgtacttag aggtacaaat                                                 20

<210> SEQ ID NO 29
<211> LENGTH: 19
<212> TYPE: DNA
<213> ORGANISM: Artificial Sequence
<220> FEATURE:
<223> OTHER INFORMATION: GADD45B primer- Forward Sequence

<400> SEQUENCE: 29
tgacaacgac atcaacatc                                                  19

<210> SEQ ID NO 30
<211> LENGTH: 19
<212> TYPE: DNA
<213> ORGANISM: Artificial Sequence
<220> FEATURE:
<223> OTHER INFORMATION: GADD45B primer- Reverse Sequence

<400> SEQUENCE: 30
gtgaccagag acaatgcag                                                  19

<210> SEQ ID NO 31
<211> LENGTH: 22
<212> TYPE: DNA
<213> ORGANISM: Artificial Sequence
```

```
<220> FEATURE:
<223> OTHER INFORMATION: PIM1 primer- Forward Sequence

<400> SEQUENCE: 31
ggcgccgggc aaagagaagg ag                                              22

<210> SEQ ID NO 32
<211> LENGTH: 24
<212> TYPE: DNA
<213> ORGANISM: Artificial Sequence
<220> FEATURE:
<223> OTHER INFORMATION: PIM1 primer- Reverse Sequence

<400> SEQUENCE: 32
acccgaagtc gatgagtttg attt                                            24

<210> SEQ ID NO 33
<211> LENGTH: 20
<212> TYPE: DNA
<213> ORGANISM: Artificial Sequence
<220> FEATURE:
<223> OTHER INFORMATION: p16 primer- Forward Sequence

<400> SEQUENCE: 33
caacgcaccg aatagttacg                                                 20

<210> SEQ ID NO 34
<211> LENGTH: 18
<212> TYPE: DNA
<213> ORGANISM: Artificial Sequence
<220> FEATURE:
<223> OTHER INFORMATION: p16 primer- Reverse Sequence

<400> SEQUENCE: 34
cagctcctca gccaggtc                                                   18
```